US006875767B2

(12) United States Patent
Bilodeau et al.

(10) Patent No.: US 6,875,767 B2
(45) Date of Patent: Apr. 5, 2005

(54) (5-CYANO-2-THIAZOLYL)AMINO-4-PYRIDINE TYROSINE KINASE INHIBITORS

(75) Inventors: Mark T. Bilodeau, Landsdale, PA (US); George D. Hartman, Landsdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 47 days.

(21) Appl. No.: 10/174,774

(22) Filed: Jun. 19, 2002

(65) Prior Publication Data

US 2003/0100567 A1 May 29, 2003

Related U.S. Application Data

(60) Provisional application No. 60/300,245, filed on Jun. 22, 2001.

(51) Int. Cl.$^7$ .................. C07D 417/14; A11K 31/495; A61K 31/444
(52) U.S. Cl. .................. 514/253.1; 514/318; 514/342; 544/364; 546/193; 546/270.7
(58) Field of Search .............................. 514/12, 253.1, 514/318, 331, 340, 341, 342; 544/364; 546/193, 270.4, 270.7

(56) References Cited

U.S. PATENT DOCUMENTS

| | | |
|---|---|---|
| 4,649,146 A | 3/1987 | Takaya et al. |
| 4,788,195 A | 11/1988 | Torley et al. |
| 4,876,252 A | 10/1989 | Torley et al. |
| 5,463,071 A | 10/1995 | Himmelsbach et al. |
| 5,516,775 A | 5/1996 | Zimmermann et al. |
| 5,521,184 A | 5/1996 | Zimmermann |
| 5,530,000 A | 6/1996 | Sanfilippo et al. |
| 5,863,924 A | 1/1999 | Berger et al. |
| 5,952,331 A | 9/1999 | Berger et al. |
| 5,958,934 A | 9/1999 | Berger et al. |
| 6,586,423 B2 * | 7/2003 | Bilodeau et al. ....... 514/217.04 |
| 6,586,424 B2 * | 7/2003 | Bilodeau et al. ....... 514/217.04 |

FOREIGN PATENT DOCUMENTS

| | | |
|---|---|---|
| DE | 19548415 | 12/1995 |
| DE | 19824175 A1 | 5/1998 |
| EP | 0 384 250 | 8/1990 |
| EP | 0 564 409 A1 | 10/1993 |
| JP | 6475475 A | 3/1989 |
| JP | 7149745 A | 6/1995 |
| WO | WO 94/01423 | 1/1994 |
| WO | WO 95/09847 | 4/1995 |
| WO | WO 95/09852 | 4/1995 |
| WO | WO 95/35275 | 12/1995 |
| WO | WO 95/35276 | 12/1995 |
| WO | WO 97/19065 | 5/1997 |
| WO | WO97/44326 | 11/1997 |
| WO | WO 99/64418 | 12/1999 |
| WO | WO 99/65884 | 12/1999 |
| WO | WO 00/09495 | 2/2000 |
| WO | WO 00/12497 | 3/2000 |
| WO | WO 00/62778 | 10/2000 |

OTHER PUBLICATIONS

Rosen LS., Hematol Oncol Clin North Am. 2002 Oct.; 16(5):1173–87., Medline Abstract PMID: 12512388.*
Wedge, S.R. et al, Cancer Research 60, 970–975, Feb. 15, 2000.*
Lutton, A. et al, Annals of the New York Academy of Sciences 979:80–93 (2002).*
Oncogene, vol. 5, pp. 519–524 (1990), by M. Shibuya, et al.
FEBS Letters, vol. 473, pp. 161–164 (2000), by M. Nakagawa, et al.
Stem Cells, vol. 12, pp. 1–6 (1994), by T. R. Burke, Jr.
Molecular Cell, vol. 4, pp. 915–924 (1999), by B. Eliceiri, et al.
Oncogene, vol. 6, pp. 1677–1683 (1991), by B. Terman, et al.
Nature Medicine, vol. 5, No. 6, pp. 623–628 (1999), by H. Gerber, et al.
Nature Biotech., vol. 17, pp. 963–968 (1999), by V. Brower.
J. of Clin. Investigation, vol. 104, No. 11, pp. 1613–1620 (1999), by N. van Bruggen, et al.
Drug News Perspect, vol. 11, No. 5, pp. 265–270 (1998), by D. A. Greenberg.
Nature, vol. 407, pp. 242–248 (2000), by G. Yancopoulos, et al.
Nature, vol. 407, pp. 249–257 (2000), by P. Carmeliet, et al.
Platelets, vol. 10, pp. 285–292 (1999), by A. Amirkhosravi, et al.
Endocrinology, Abstract, vol. 141, No. 5, pp. 1667–1674 (2000), by M. Deckers, et al.
Chem. Abst., vol. 109, No. 8, p. 634 (1988), N. A. Shvink.
Chem. Abstr., vol. 111, No. 15 (1989), by M. Tsuji.
Chem. Abstr., vol. 111, No. 21 (1989), by M. Santus.
Chem. Abstr., vol. 126, No. 21 (1997), by C. S. Ra.
Chem. Abstr., vol. 101, No. 11 (1984), by H. Nagatomi.

(Continued)

Primary Examiner—Thomas C. McKenzie
(74) Attorney, Agent, or Firm—David A. Muthard; Mark R. Daniel

(57) ABSTRACT

The present invention relates to compounds having the formula I:

which inhibit, regulate and/or modulate tyrosine kinase signal transduction, compositions which contain these compounds, and methods of using them to treat tyrosine kinase-dependent diseases and conditions. The compounds of the present invention are useful in treating angiogenesis, cancer, tumor growth, atherosclerosis, age related macular degeneration, diabetic retinopathy, inflammatory diseases, and the like in mammals.

7 Claims, No Drawings

OTHER PUBLICATIONS

Abstract, Indiana J. Chem., Sect. G (1986), 25B(4), 452–5, S.E. Kulkarni, et al.

Abstract, Eur. Pat. Appl., 35 pp., T. Takaya, et al.

Abstract, Acta Pol. Pharm. (1980), 37(3), 293–300, M. Santus.

Abstract, Res. Commun., (1982), 14(4), 359–68, M. Tandon, et al.

Abstract, Pharmazie (1975), 30(3), 141–7, G. Wagner, et al.

Annual Reports in Med. Chem., vol. 27, pp. 139–148 (1992), Mitchell, et al.

* cited by examiner

(5-CYANO-2-THIAZOLYL)AMINO-4-PYRIDINE TYROSINE KINASE INHIBITORS

RELATED APPLICATIONS

This application claims the benefit of priority of U.S. Provisional Application No. 60/300,245, filed on Jun. 22, 2001.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates. Tyrosine kinases play critical roles in signal transduction for a number of cell functions via substrate phosphorylation. Though the exact mechanisms of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene*, 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, *J. Cell Biol.* 129:895–898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11–15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, *Cytokine & Growth Factor Reviews* 7:259–270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Thienyl-amino pyridines have been previously reported to be useful in the treatment of cancer via inhibition of tyrosine kinase. (See, WO 01/17995 A1; published 15 Mar. 2001). The need still remains, however, to develop compounds with improved pharmaceutical activity. Accordingly, the identification of small compounds with enhanced pharmocokinteic properties which inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof:

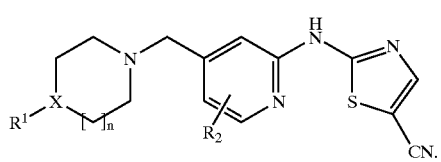

I

DETAILED DESCRIPTION OF THE INVENTION

The compounds of this invention are useful in the inhibition of kinases and are illustrated by a compound of Formula I:

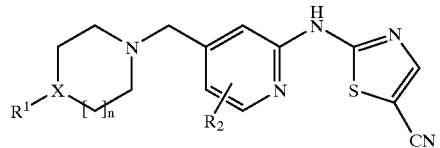

I or a pharmaceutically acceptable salt or stereoisomer thereof, wherein n is or 1;

X is C—H or N,
  provided X is C—H if n=1 and $R^1$ is $SO_2$—$(C_1-C_6$ alkyl) and provided that X is C—H if $R^1$ is $NH(C=O)NR^3H$;

$R^1$ is
  1) $SO_2$—$(C_1-C_6$ alkyl),
  2) $(C=O)NR^3H$, or
  3) $NH(C=O)NR^3H$;

$R^2$ is
  1) H,
  2) OH,
  3) $OC_1-C_6$ alkyl,
  4) $C_1-C_6$ alkyl, or
  5) halo; and $R^3$ is $C_1-C_6$ alkyl.

A second embodiment is the compound of Formula I described above, or a pharmaceutically acceptable salt thereof, wherein n is 1; X is N; and $R^1$ is $(C=O)NR^3H$.

A further embodiment is compound selected from:
4-[2-(5-cyano-thiazol-2-ylamino)-pyridin-4-ylmethyl]-piperazine-1-carboxylic acid methylamide;
2-[(4-{[4-(methylsulfonyl)piperidin-1-yl]methyl}pyridin-2-yl)amino]-1,3-thiazole-5-carbonitrile;
N-[(3R)-1-({2-[(5-cyano-1,3-thiazol-2-yl)amino]pyridin-4-yl}methyl)pyrrolidin-3-yl]-N'-methylurea;
2-({1-[((1Z,2E)-3-methyl-4-{[(3S)-5-oxopyrrolidin-3-yl]amino}but-2-enylidene)amino]vinyl}amino)-1,3-thiazole-5-carbonitrile;
4-[2-(5-cyano-thiazol-2-ylamino)-5-methyl-pyridin-4-ylmethyl]-piperazine-1-carboxylic acid methylamide;
4-[2-(5-cyano-thiazol-2-ylamino)-3-methyl-pyridin-4-ylmethyl]-piperazine-1-carboxylic acid methylamide;
4-({2-chloro-6-[(5-cyano-1,3-thiazol-2-yl)amino]pyridin-4-yl}methyl)-N-methylpiperazine-1-carboxamide;
4-({2-[(5-cyano-1,3-thiazol-2-yl)amino]-6-ethylpyridin-4-yl}methyl)-N-methylpiperazine-1-carboxamide; and
2-({4-[(4-acetylpiperazin-1-yl)methyl]-6-methylpyridin-2-yl}amino)-1,3-thiazole-5-carbonitrile; or a pharmaceutically acceptable salt or stereoisomer thereof.

A specific embodiment of the invention is a compound which is:

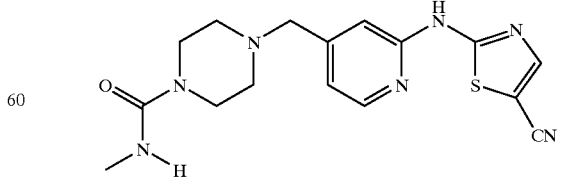

4-[2-(5-cyano-thiazol-2-ylamino)-pyridin-4-ylmethyl]-piperazine-1-carboxylic acid methylamide, or a pharmaceutically acceptable salt thereof.

A second specific embodiment is a compound which is:

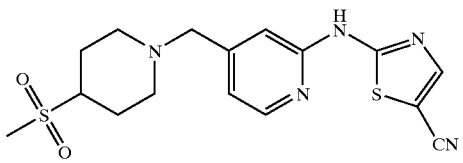

2-[(4-{[4-(methylsulfonyl)piperidin-1-yl]methyl}pyridin-2-yl)amino]-1,3-thiazole-5-carbonitrile, or a pharmaceutically acceptable salt thereof.

Another specific embodiment of the invention is illustrated by a compound which is:

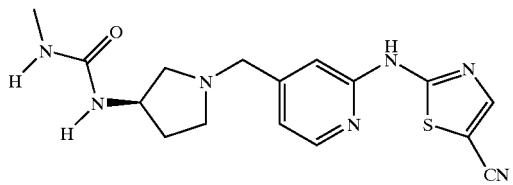

N-[(3R)-1-({2-[(5-cyano-1,3-thiazol-2-yl)amino]pyridin-4-yl}methyl)pyrrolidin-3-yl]-N'-methylurea, or a pharmaceutically acceptable salt or stereoisomer thereof.

And yet a further specific embodiment is a compound which is:

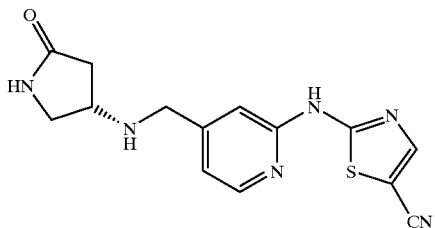

2-({1-[((1Z,2E)-3-methyl-4-{[(3S)-5-oxopyrrolidin-3-yl]amino}but-2-enylidene)amino]vinyl}amino)-1,3-thiazole-5-carbonitrile, or a pharmaceutiaclly acceptable salt or stereoisomer thereof.

Another specific embodiment is a compound which is:

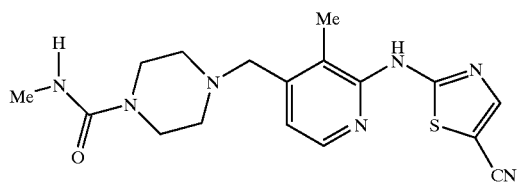

4-[2-(5-cyano-thiazol-2-ylamino)-3-methyl-pyridin-4-ylmethyl]-piperazine-1-carboxylic acid methylamide, or a pharmaceutically acceapatble salt thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The instanty disclosed compounds are inhibitors of tyrosine kinase and are therefore useful to treat or prevent tyrosine kinase-dependent diseases or conditions in mammals.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like). In treating such conditions with the instantly claimed compunds, the required therapeutic amount will vary according to the specific disease and is readily ascertainable by those skilled in the art. Although both treatment and prevention are contemplated by the scope of the invention, the treatment of these conditions is the preferred use.

The present invention encompasses a method of treating or preventing cancer in a mammal in need of such treatment which is comprised of administering to said mammal a therapeutically effective amount of a compound of Formula I. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, glioblastomas and breast carcinoma. The utility of angiogenesis inhibitors in the treatment of cancer is known in the literature, see J. Rak et al. *Cancer Research*, 55:4575–4580, 1995, for example. The role of angiogenesis in cancer has been shown in numerous types of cancer and tissues: breast carcinoma (G. Gasparini and A. L. harris, *J. Clin. Oncol.*, 1995, 13:765–782; M. Toi et al., *Japan. J. Cancer Res.*, 1994, 85:1045–1049); bladder carcinomas (A. J. Dickinson et al., *Br. J. Urol.*, 1994, 74:762–766); colon carcinomas (L. M. Ellis et al., *Surgery*, 1996, 120(5):871–878); and oral cavity tumors (J. K. Williams et al., *Am. J. Surg.*, 1994, 168:373–380).

Tumors which have undergone neovascularization show an increased potential for metastasis. VEGF released from cancer cells enhances metastasis possibly by increasing extravasation at points of adhesion to vascular endothelium. (A. Amirkhosravi et al., *Platelets*, 10:285–292 (1999)). In fact, angiogenesis is essential for tumor growth and metastasis. (S. P. gunningham, et al., *Can. Research*, 61: 3206–3211 (2001)). The angiogenesis inhibitors disclosed in the present application are therefore also useful to prevent or decrease tumor cell metastasis. Such a use is also contemplated to be within the scope of the present invention.

Further included within the scope of the invention is a method of treating or preventing a disease in which angiogenesis is implicated, which is comprised of administering to a mammal in need of such treatment a therapeutically effective amount of a compound of Formula I. Ocular neovascular diseases are an example of conditions where much of the resulting tissue damage can be attributed to aberrant infiltration of blood vessels in the eye. (see WO 00/30651, published 2 Jun. 2000). The undesireable infiltration can be triggered by ischemic retinopathy, such as that resulting from diabetic retinopathy, retinopathy of prematurity, retinal vein occlusions, etc., or by degenerative diseases, such as the choroidal neovascularization obeserved in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formual I. Examples of such inflammatory diseases are rheumatoid arthritis, psoriasis, contact dermatitis, delayed hypersensitivity reactions, and the like. (A. Giatromanolaki et al., *J. Pathol.* 2001; 194:101–108).

Also included within the scope of the present invention is a method of treating or preventing bone associated pathologies selected from osteosarcoma, osteoarthritis, and rickets, also known as oncogenic osteomalacia. (Hasegawa et al., *Skeletal Radiol.*, 28, pp.41–45, 1999; Gerber et al., *Nature Medicine*, Vol. 5, No. 6, pp.623–628, June 1999). And since VEGF directly promotes osteoclastic bone resorption through KDR/Flk-1 expressed in mature osteoclasts (FEBS Let. 473:161–164 (2000); *Endocrinology*, 141:1667 (2000)), the instant compounds are also useful to treat and prevent conditions related to bone resorption, such as osteoporosis and Paget's disease.

A method of treating or preventing preeclampsia is also within the which comprises administering a therapeutically effective amount of a compound of Formula I. Studies have shown that the action of VEGF on the Flt-1 receptor is pivotal in the pathogenesis of preeclampsia. (*Laboratory Investigation* 79:1101–1111 (September 1999)). Vessels of pregnant women incubated with VEGF exhibit a reduction in endothelium-dependent relaxation similar to that induced by plasma from women with preeclampsia. In the presence of an anti-Flt-1 receptor antibody, however, neither VEGF or plasma from women with preeclampsia reduced the endothelium-dependent relaxation. Therefore the claimed compounds serve to treat preeclampsia via their action on the tyrosine kinase domain of the Flt-1 receptor.

Also within the scope of the invention is a method of reducing or preventing tissue damage following a cerebral ischemic event which comprises administering a therapeutically effective amount of a compound of Formula I. The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999); *Nature Med* 7:222–227 (2001)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art (see WO 00/61186).

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS 188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl] acridine-2-(6H) propanamine, 1-amino-9-ethyl-5-fluoro-2,3-dihydro-9-hydroxy-4-methyl-1H, 12H-benzo[de]pyrano[3',4':b,7]indolizino[1,2b]quinoline-10,13(9H,15H)dione, lurtotecan, 7-[2-(N-isopropylamino)ethyl]-(20S) camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido [4,3-b]carbazole-1-carboxamide, asulacrine, (5a, 5aB, 8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl) amino]benzo[g]isoguinoline-5,10-dione, 5-(3-aminopropylamino)-7,10-dihydroxy-2-(2-hydroxyethyl-aminomethyl)-6H-pyrazolo[4,5,1-de]acridin-6-one, N-[1-[2 (diethylamino)ethylamino]-7-methoxy-9-oxo-9H-thioxanthen-4-ylmethyl]formamide, N-(2-(dimethylamino) ethyl)acridine-4-carboxamide, 6-[[2-(dimethylamino)ethyl] amino]-3-hydroxy-7H-indeno[2,1-c]quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II:

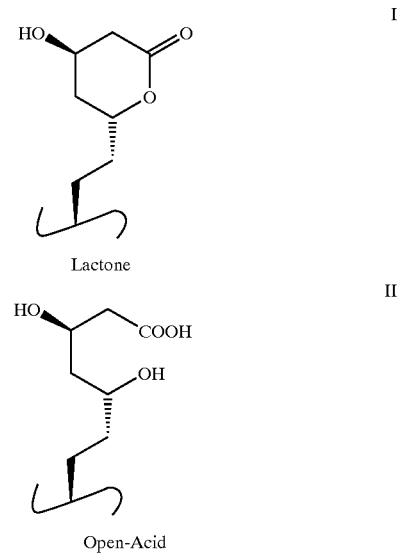

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl] piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9,12]oxatriazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp.1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p.573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)fumagillol, thalidomide, angiostatin, troponin-1, angiotensin II antagonists (see Fernandez et al., J. Lab. Clin. Med. 105:141–145 (1985)), and antibodies to VEGF (see, Nature Biotechnology, Vol. 17, pp.963–968 (October 1999); Kim et al., Nature, 362, 841–844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 μM or less as measured by the cell or microsomal assay disclosed herein.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by the cell or micromsal assay disclosed hereinunder. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604, 260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932, 598, issued Aug. 3, 1999, all of which are hereby incorporated by reference.

Other examples of specific inhibitors of COX-2 include the following:

3-(3-fluorophenyl)-4-(4-(methylsulfonyl)phenyl)-2-(5H)-furanone;
3-(3,4-difluorophenyl)-4-(4-(methylsulfonyl)phenyl)-2-(5H)-furanone;
3-(3,4-dichlorophenyl)-4-(4-(methylsulfonyl)phenyl)-2-(5H)-furanone;
3-phenyl-4-(4-(methylsulfonyl)phenyl)-2-(5H)-furanone;
5,5-dimethyl-3-(3-fluorophenyl)-4-(methylsulfonyl)phenyl)-2-(5H)-furanone;
3-(4-methylsulfonyl)phenyl-2-phenyl-5-trifluoromethyl-pyridine;
2-(3-chlorophenyl)-3-(4-methylsulfonyl)phenyl-5-trifluoromethyl-pyridine;
2-(4-chlorophenyl)-3-(4-methylsulfonyl)phenyl-5-trifluoromethyl-pyridine;
2-(4-fluorophenyl)-3-(4-methylsulfonyl)phenyl-5-trifluoromethyl-pyridine;
3-(4-methylsulfonyl)phenyl-2-(3-pyridinyl)-5-trifluoromethylpyridine;
5-methyl-3-(4-methylsulfonyl)phenyl-2-phenylpyridine;
2-(4-chlorophenyl)-5-methyl-3-(4-methylsulfonyl)phenylpyridine;
5-methyl-3-(4-methylsulfonyl)phenyl-2-(3-pyridinyl)pyridine;
5-chloro-2-(4-chlorophenyl)-3-(4-methylsulfonyl)phenylpyridine;
5-chloro-3-(4-methylsulfonyl)phenyl-2-(2-pyridinyl)pyridine;
5-chloro-3-(4-methylsulfonyl)phenyl-2-(3-pyridinyl)pyridine;
5-chloro-3-(4-methylsulfonyl)phenyl-2-(4-pyridinyl)pyridine;
5-chloro-3-(4-methylsulfonyl)phenyl-2-(2-methyl-5-pyridinyl)pyridine;
2-(4-chlorophenyl)-3-(4-methylsulfonyl)phenylpyridinyl-5-carboxylic acid methyl ester;
2-(4-chlorophenyl)-3-(4-methylsulfonyl)phenylpyridinyl-5-carboxylic acid;
5-cyano-2-(4-chlorophenyl)-3-(4-methylsulfonyl)phenylpyridine;
5-chloro-3-(4-methylsulfonyl)phenyl-2-(3-pyridyl)pyridine hydromethanesulfonate;
5-chloro-3-(4-methylsulfonyl)phenyl-2-(3-pyridyl)pyridine hydrochloride;
5-chloro-3-(4-methylsulfonyl)phenyl-2-(2-methyl-5-pyridinyl)pyridine hydrochloride;
5-chloro-3-(4-methylsulfonyl)phenyl-2-(2-ethyl-5-pyridinyl)pyridine;
5-chloro-3-(4-methylsulfonyl)phenyl-2-(2-ethyl-5-pyridinyl)pyridine hydromethanesulfonate;
3-(3,4-difluorophenoxy)-5,5-dimethyl-4-(4-(methylsulfonyl)phenyl)-5H-furan-2-one;
3-(3-fluorophenoxy)-5,5-dimethyl-4-(4-(methylsulfonyl)phenyl)-5H-furan-2-one;
3-(3,5-difluorophenoxy)-5,5-dimethyl-4-(4-(methylsulfonyl)phenyl)-5H-furan-2-one;
3-phenoxy-5,5-dimethyl-4-(4-(methylsulfonyl)phenyl)-5H-furan-2-one;
3-(2,4-difluorophenoxy)-5,5-dimethyl-4-(4-(methylsulfonyl)phenyl)-5H-furan-2-one;
3-(4-chlorophenoxy)-5,5-dimethyl-4-(4-(methylsulfonyl)phenyl)-5H-furan-2-one;
3-(3,4-dichlorophenoxy)-5,5-dimethyl-4-(4-(methylsulfonyl)phenyl)-5H-furan-2-one;
3-(4-fluorophenoxy)-5,5-dimethyl-4-(4-(methylsulfonyl)phenyl)-5H-furan-2-one;
3-(4-fluorophenylthio)-5,5-dimethyl-4-(4-(methylsulfonyl)phenyl)-5H-furan-2-one;
3-(3,5-difluorophenylthio)-5,5-dimethyl-4-(4-(methylsulfonyl)phenyl)-5H-furan-2-one;
3-phenylthio-5,5-dimethyl-4-(4-(methylsulfonyl)phenyl)-5H-furan-2-one;
3-(N-phenylamino)-5,5-dimethyl-4-(4-(methylsulfonyl)phenyl)-5H-furan-2-one;
3-(N-methyl-N-phenylamino)-5,5-dimethyl-4-(4-(methylsulfonyl)phenyl)-5H-furan-2-one;
3-cyclohexyloxy-5,5-dimethyl-4-(4-(methylsulfonyl)phenyl)-5H-furan-2-one;
3-phenylthio-4-(4-(methylsulfonyl)phenyl)-5H-furan-2-one;
3-benzyl-5,5-dimethyl-4-(4-(methylsulfonyl)phenyl)-5H-furan-2-one;
3-(3,4-difluorophenylhydroxymethyl)-5,5-dimethyl-4-(4-(methylsulfonyl)phenyl)-5H-furan-2-one;
3-(3,4-difluorobenzoyl)-5,5-dimethyl-4-(4-(methylsulfonyl)phenyl)-5H-furan-2-one;
3-benzoyl-5,5-dimethyl-4-(4-(methylsulfonyl)phenyl)-5H-furan-2-one;
4-(4-(methylsulfonyl)phenyl)-3-phenoxy-1-oxaspiro[4.4]non-3-en-2-one;
4-(4-(methylsulfonyl)phenyl)-3-phenylthio-1-oxaspiro[4,4]non-3-en-2-one;
4-(2-oxo-3-phenylthio-1-oxa-spiro[4,4]non-3-en-4-yl)benzenesulfonamide;
3-(4-fluorobenzyl)-5,5-dimethyl-4-(4-(methylsulfonyl)phenyl)-5H-furan-2-one;
3-(3,4-difluorophenoxy)-5-methoxy-5-methyl-4-(4-(methylsulfonyl)phenyl)-5H-furan-2-one;
3-(5-chloro-2-pyridyloxy)-5,5-dimethyl-4-(4-(methylsulfonyl)phenyl)-5H-furan-2-one;

3-(2-pyridyloxy)-5,5-dimethyl-4-(4-(methylsulfonyl)
    phenyl)-5H-furan-2-one;
3-(6-methyl-2-pyridyloxy)-5,5-dimethyl-4-(4-
    (methylsulfonyl)phenyl)-5H-furan-2-one;
3-(3-isoquinolinoxy)-5,5-dimethyl-4-(4-(methylsulfonyl)
    phenyl)-5H-furan-2-one;
3-(4-(methylsulfonyl)phenyl)-2-phenoxycyclopent-2-
    enone;
3-(4-(methylsulfonyl)phenyl)-2-(3,4-difluorophenoxy)
    cyclopent-2-enone;
5,5-dimethyl-4-(4-methylsulfonylphenyl)-3-(5-
    bromopyridin-2-yloxy)-5H-furan-2-one;
5,5-dimethyl-4-(4-methylsulfonylphenyl)-3-(2-propoxy)-
    5H-furan-2-one;
2-(3,4-difluorophenoxy)-3-(4-methylsulfonylphenyl)-
    cyclopent-2-enone;
3-(5-benzothiophenyloxy)-5,5-dimethyl-4-(4-
    (methylsulfonyl)phenyl)-5H-furan-2-one;
5,5-dimethyl-4-(4-methylsulfonyl-phenyl)-3-(pyridyl-4-
    oxy)-5H-furan-2-one;
5,5-dimethyl-4-(4-methylsulfonyl-phenyl)-3-(pyridyl-3-
    oxy)-5H-furan-2-one;
3-(2-methyl-5-pyridyloxy)-5,5-dimethyl-4-(4-
    (methylsulfonyl)phenyl)-5H-furan-2-one;
3-(2-fluoro-4-trifluoromethyl)phenoxy-4-(4-
    methylsulfonyl)phenyl)-5,5-dimethyl-5H-furan-2-one;
3-(5-chloro-2-pyridylthio)-5,5-dimethyl-4-(4-
    methylsulfonyl)phenyl)-5H-furan-2-one;
2-(3,5-difluorophenoxy)-3-(4-methylsulfonylphenyl)-
    cyclopent-2-enone;
3-(2-pyrimidinoxy)-5,5-dimethyl-4-(4-methylsulfonyl)
    phenyl-5H-furan-2-one;
3-(3-chloro-5-pyridyloxy)-5,5-dimethyl-4-(4-
    (methylsulfonyl)phenyl)-5H-furan-2-one;
3-(3-(1,2,5-thiadiazolyl)oxy)-4-(4-(methylsulfonyl)phenyl)-
    5,5-dimethyl-5H-furan-2-one;
3-(5-isoquinolinoxy)-5,5-dimethyl-4-(4-(methylsulfonyl)
    phenyl-5H-furan-2-one;
3-(6-amino-2-pyridyloxy)-5,5-dimethyl-4-(4-
    (methylsulfonyl)phenyl)-5H-furan-2-one;
3-(3-chloro-4-fluoro)phenoxy-4-(methylsulfonyl)phenyl)-5,
    5-dimethyl-5H-furan-2-one;
3-(6-quinolinoxy)-5,5-dimethyl-4-(4-(methylsulfonyl)
    phenyl)-5H-furan-2-one;
3-(5-nitro-2-pyridyloxy)-5,5-dimethyl-4-(4-methylsulfonyl)
    phenyl-5H-furan-2-one;
3-(2-thiazolylthio)-5,5-dimethyl-4-(4-(methylsulfonyl)
    phenyl)-5H-furan-2-one;
3-(3-chloro-5-pyridyloxy)-5,5-dimethyl-4-(4-
    (methylsulfonyl)phenyl)-5H-furan-2-one;
5,5-dimethyl-4-(4-methylsulfonylphenyl)-3-(2-propoxy)-
    5H-furan-2-one;
3-(3-trifluoromethyl)phenoxy-4-(4-(methylsulfonyl)phenyl)-
    5,5-dimethyl-5H-furan-2-one;
5,5-dimethyl-(4-(4-(methylsulfonyl)phenyl)-3-(piperidine-1-
    carbonyl)-5-H-furan-2-one;
5,5-dimethyl-3-(2-Butoxy)-4-(4-methylsulfonylphenyl)-
    5H-furan-2-one;
5,5-dimethyl-4-(4-methylsulfonylphenyl)-3-(3-pentoxy)-
    5H-furan-2-one;
2-(5-chloro-2-pyridyloxy)-3-(4-methylsulfonyl)
    phenylcyclopent-2-enone;
3-(4-methyl-2-pyridyloxy)-5,5-dimethyl-4-(4-
    methylsulfonyl)phenyl)-5H-furan-2-one;
(5R)-3-(3,4-difluorophenoxy)-5-ethyl-5-methyl-4-(4-
    methylsulfonyl)phenyl-5H-furan-2-one;
(5R)-3-(4-chlorophenoxy)-5-ethyl-5-methyl-4-(4-
    methylsulfonyl)phenyl-5H-furan-2-one;
3-(2-methyl-3-pyridyloxy)-5,5-dimethyl-4-(4-
    methylsulfonyl)phenyl-5H-furan-2-one;
3-(4-methyl-5-nitro-2-pyridyloxy)-5,5-dimethyl-4-(4-
    methylsulfonyl)phenyl-5H-furan-2-one;
3-(5-chloro-4-methyl-2-pyridyloxy)-5,5-dimethyl-4-(4-
    methylsulfonyl)phenyl-5H-furan-2-one;
3-(5-fluoro-4-methyl-2-pyridyloxy)-5,5-dimethyl-4-(4-
    methylsulfonyl)phenyl-5H-furan-2-one;
3-(3-chloro-2-pyridyloxy)-5,5-dimethyl-4-(4-
    methylsulfonyl)phenyl-5H-furan-2-one;
3-(4-fluorophenoxy)-5-methyl-4-(4-methylsulfonyl)phenyl-
    5-propyl-5H-furan-2-one;
3-(N,N-diethylamino)-5,5-dimethyl-4-(4-(methylsulfonyl)
    phenyl)-5H-furan-2-one;
5,5-dimethyl-4-(4-methylsulfonyl-phenyl)-3-(3,5-dichloro-
    2-pyridyloxy)-5H-furan-2-one;
(5R)-3-(4-bromophenoxy)-5-ethyl-5-methyl-4-(4-
    methylsulfonyl)phenyl-5H-furan-2-one;
(5R)-3-(4-methoxyphenoxy)-5-ethyl-5-methyl-4-(4-
    methylsulfonyl)phenyl-5H-furan-2-one;
(5R)-3-(5-chloro-2-pyridyloxy)-5-methyl-4-(4-
    methylsulfonyl)phenyl-5-(2,2,2-trifluoroethyl)-5H-furan-
    2-one;
3-(5-chloro-2-pyridyloxy)-5-methyl-4-(4-methylsulfonyl)
    phenyl-5-propyl-5H-furan-2-one;
3-(1-cyclopropyl-ethoxy)-5,5-dimethyl-4-(4-
    methylsulfonyl)phenyl)-5H-furan-2-one;
5-methyl-4-(4-(methylsulfonyl)phenyl)-3-(2-(propoxy)-5-
    (2-trifluoroethyl)-5H-furan-2-one;
5(R)-5-ethyl-5-methyl-4-(4-(methylsulfonyl)phenyl)-3-(2-
    propoxy)-5H-furan-2-one;
5,5-dimethyl-3-(2,2-dimethylpropyloxy)-4-(4-
    (methylsulfonyl)phenyl)-5H-furan-2-one;
5(R)-3-(1-cyclopropyl-ethoxy)-5-ethyl-5-methyl-4-(4-
    (methylsulfonyl)phenyl)-5H-furan-2-one;
5(S)-5-ethyl-5-methyl-4-(4-(methylsulfonyl)phenyl)-3-(2-
    propoxy)-5H-furan-2-one;
3-(1-cyclopropylethoxy)-5,5-dimethyl-4-(4-
    (methylsulfonyl)phenyl)-5H-furan-2-one;
3-(1-cyclopropylethoxy)-5,5-dimethyl-4-(4-
    (methylsulfonyl)phenyl)-5H-furan-2-one;
5,5-dimethyl-3-(isobutoxy)-4-(4-(methylsulfonyl)phenyl)-
    5H-furan-2-one;
3-(4-bromophenoxy)-5,5-dimethyl-4-(4-(methylsulfonyl)
    phenyl)-5H-furan-2-one;
3-(2-quinolinoxy)-5,5-dimethyl-4-(4-(methylsulfonyl)
    phenyl)-5H-furan-2-one;
3-(2-chloro-5-pyridyloxy)-5,5-dimethyl-4-(4-
    (methylsulfonyl)phenyl)-5H-furan-2-one;
3-(6-benzothiazolyloxy)-5,5-dimethyl-4-(4-
    (methylsulfonyl)phenyl)-5H-furan-2-one;
3-(6-chloro-2-pyridyloxy)-5,5-dimethyl-4-(4-
    (methylsulfonyl)phenyl)-5H-furan-2-one;
3-(4-quinazolyloxy)-5,5-dimethyl-4-(4-(methylsulfonyl)
    phenyl)-5H-furan-2-one;
(5R)-3-(5-fluoro-2-pyridyloxy)-5-ethyl-5-methyl-4-(4-
    methylsulfonyl)phenyl-5H-furan-2-one;
(5R)-3-(4-fluorophenoxy)-5-ethyl-5-methyl-4-(4-
    methylsulfonyl)phenyl-5H-furan-2-one;
(5R)-3-(5-fluoro-2-pyridyloxy)-5-methyl-4-(4-
    methylsulfonyl)phenyl-5-(2,2,2-trifluoroethyl)-5H-furan-
    2-one;

3-(1-isoquinolinyloxy)-5,5-dimethyl-4-(methylsulfonyl)
   phenyl-5H-furan-2-one;
(5R)-3-(4-fluorophenoxy)-5-methyl-4-(4-methylsulfonyl)
   phenyl-5-(2,2,2-trifluoroethyl)-5H-furan-2-one;
3-(3-fluoro-2-pyridyloxy)-5,5-dimethyl-4-(4-
   methylsulfonyl)phenyl-5H-furan-2-one;
(5R)-3-(3,4-difluorophenoxy)-5-methyl-4-(4-
   methylsulfonyl)phenyl-5-(2,2,2-trifluoroethyl)-5H-furan-
   2-one;
(5R)-3-(5-chloro-2-pyridyloxy)-5-ethyl-5-methyl-4-(4-
   methylsulfonyl)phenyl-5H-furan-2-one;
3-(3,4-difluorophenoxy)-5-methyl-5-trifluoromethyl-4-(4-
   methylsulfonyl)phenyl-5H-furan-2-one;
3-(3,4-difluorophenoxy)-5-methyl-4-(4-(methylsulfonyl)
   phenyl)-5-propyl-5H-furan-2-one;
3-cyclobutyloxy-5,5-dimethyl-4-(4-methylsulfonylphenyl-
   5H-furan-2-one;
3-(1-indanyloxy)-5,5-dimethyl-4-(4-(methylsulfonyl)
   phenyl)-5H-furan-2-one;
3-(2-indanyloxy)-5,5-dimethyl-4-(4-methylsulfonyl)
   phenyl)-5H-furan-2-one;
3-cyclopentyloxy-5,5-dimethyl-4-(4-methylsulfonylphenyl)
   ₅H-furan-2-one;
3-(3,3-dimethylcyclopentyloxy)-5,5-dimethyl-4-(4-
   methylsulfonyl-phenyl)-5H-furan-2-one;
3-isopropoxy-5-methyl-4-(4-methylsulfonylphenyl)-5-
   propyl-5H-furan-2-one;
3-(2-methoxy-5-pyridyloxy)-5,5-dimethyl-4-(4-
   methylsulfonyl)phenyl-5H-furan-2-one;
3-(5-methyl-2-pyridyloxy)-5,5-dimethyl-4-(4-
   methylsulfonyl)phenyl-5H-furan-2-one;
(5RS)-3-(3,4-difluorophenoxy)-5-methyl-4-(4-
   methylsulfonyl)phenyl-5-(2,2,2-trifluoroethyl)-5H-furan-
   2-one;
3-(3-chloro-4-methoxyphenoxy)-5,5-dimethyl-4-(4-
   methylsulfonyl)phenyl-5H-furan-2-one;
(5R)-3-(3-chloro-4-methoxyphenoxy)-5-ethyl-5-methyl-4-
   (4-methylsulfonyl)phenyl-5H-furan-2-one;
(5R)-3-(4-chlorophenoxy)-5-trifluoroethyl-5-methyl-4-(4-
   methylsulfonyl)phenyl-5H-furan-2-one;
(5R)-3-(4-bromophenoxy)-5-trifluoroethyl-5-methyl-4-(4-
   methylsulfonyl)phenyl-5H-furan-2-one;
5-cyclopropylmethyl-3-(3,4-difluorophenoxy)-5-methyl-(4-
   methylsulfonyl)phenyl-5H-furan-2-one;
(5R)-3-(3-fluorophenoxy)-5-ethyl-5-methyl-4-(4-
   methylsulfonyl)phenyl-5H-furan-2-one;
(5R)-3-(4-chloro-3-fluorophenoxy)-5-ethyl-5-methyl-4-(4-
   methylsulfonyl)phenyl-5H-furan-2-one;
(5R)-3-phenoxy-5-ethyl-5-methyl-4-(4-methylsulfonyl)
   phenyl-5H-furan-2-one;
(5R)-3-(4-chloro-3-methylphenoxy)-5-ethyl-5-methyl-4-(4-
   methylsulfonyl)phenyl-5H-furan-2-one;
3-(4-chloro-3-methylphenoxy)-5-5-dimethyl-4-(4-
   methylsulfonyl)phenyl-5H-furan-2-one;
(5R)-3-(5-bromo-2-pyridyloxy)-4-(4-methylsulfonylphen-
   yl)-5-methyl-5-(2,2,2-trifluoroethyl)-5H-furan-2-one;
(5R)-3-(5-bromo-2-pyridyloxy)-4-(4-methylsulfonylphen-
   yl)-5-ethyl-5-methyl-5H-furan-2-one;
3-(5-chloro-6-methyl-2-pyridyloxy)-5,5-dimethyl-4-(4-
   methylsulfonyl)phenyl-5H-furan-2-one;
3-(5-cyclopropyl-2-pyridyloxy)-5,5-dimethyl-4-(4-
   methylsulfonyl)phenyl-5H-furan-2-one;
3-(1-cyclopropylethoxy)-4-(4-methylsulfonyl)phenyl-5H-
   furan-2-one; and
3-(cyclopropylmethoxy)-4-(4-methylsulfonyl)phenyl-5H-
   furan-2-one;

or a pharmaceutically acceptable salt or stereoisomer thereof.

Inhibitors of COX-2 that are particularly useful in the instant method of treatment are:

3-phenyl-4-(4-(methylsulfonyl)phenyl)-2-(5H)-furanone; and

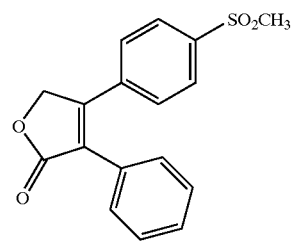

5-chloro-3-(4-methylsulfonyl)phenyl-2-(2-methyl-5-pyridinyl)pyridine;

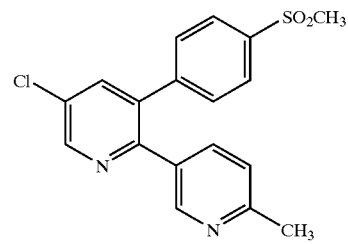

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

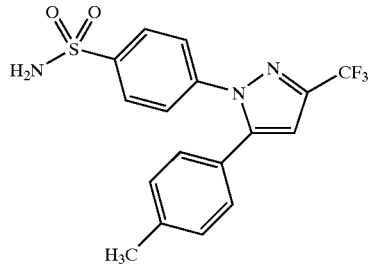

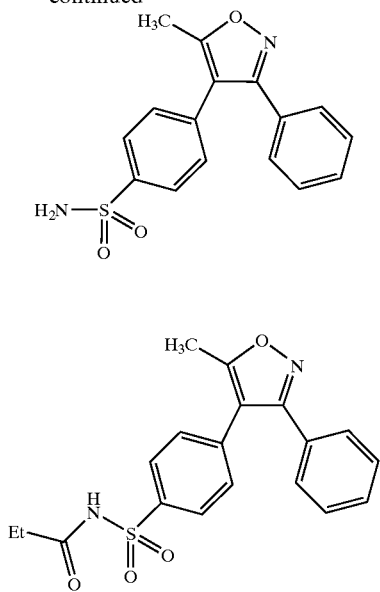

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RP14610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The scope of the invetion therefore encompasses the use of the instantly claimed compounds in combination with a second compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors to be useed as the second compound are a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. Preferred estrogen receptor modulators are tamoxifen and raloxifene.

Also included in the scope of the claims is a method of treating cancer which comprises administering a therapeutically effective amount of a compound of Formula I in combination with radiation therapy and/or in combination with a compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formual I in combination with paclitaxel or trastuzumab.

The invention further encompasses a method of treating or preventing cancer which comprises administering a therapeutically effective amount of a compound of Formula I in combination with a COX-2 inhibitor.

These and other aspects of the invention will be apparent from the teachings contained herein.

Definitions

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

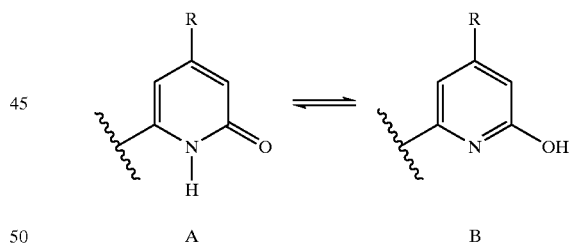

Lines drawn into the ring systems from substituents indicate that the indicated bond may be attached to any of the substitutable ring carbon atoms. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

As used herein, "alkyl" is intended to include both branched, straight-chain, and cyclic saturated aliphatic hydrocarbon groups having the specified number of carbon atoms. For example, $C_1$–$C_6$, as in "$C_1$–$C_6$ alkyl" is defined to include groups having 1, 2, 3, 4, 5, or 6 carbons in a linear, branched, or cyclic arrangement. For example, "$C_1$–$C_6$ alkyl" specifically includes methyl, ethyl, propyl, butyl, pentyl, hexyl, and so on, as well as cycloalkyls such as cyclopropyl, cyclobutyl, cyclopentyl, cyclohexyl, methylenecylopentyl, and so on.

As appreciated by those of skill in the art, "halo" or "halogen" as used herein is intended to include chloro, fluoro, bromo and iodo.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Similarly, the salts of the acidic compounds are formed by reactions with the appropriate inorganic or organic base.

Assays

The compounds of the instant invention described in the Examples were tested by the assays described below and were found to have kinase inhibitory activity. Other assays are known in the literature and could be readily performed by those of skill in the art (see, for example, Dhanabal et al., *Cancer Res.* 59:189–197; Xin et al., *J. Biol. Chem.* 274:9116–9121; Sheu et al., *Anticancer Res.* 18:4435–4441; Ausprunk et al., *Dev. Biol.* 38:237–248; Gimbrone et al., *J. Natl. Cancer Inst.* 52:413–427; Nicosia et al., *In Vitro* 18:538–549).

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in *Spodoptera frugiperda* (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsuflonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10× Substrate: 750 μg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.

2. Add 35 μl of reaction mix containing 5 μl of 10× reaction buffer, 5 μl 25 mM ATP/10 μCi [$^{33}$P]ATP (Amersham), and 5 μl 10× substrate.

3. Start the reaction by the addition of 10 μl of KDR (25 nM) in enzyme dilution buffer.

4. Mix and incubate at room temperature for 15 minutes.

5. Stop by the addition of 50 μl stop solution.

6. Incubate for 15 minutes at 4° C.

7. Transfer a 90 μl aliquot to filter plate.

8. Aspirate and wash 3 times with wash solution.

9. Add 30 μl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 3–7 below.

Culture Plates: NUNCLON 96-well polystyrene tissue culture plates (NUNC #167008).

Assay Medium: Dulbecco's modification of Eagle's medium containing 1 g/mL glucose (low-glucose DMEM; Mediatech) plus 10% (v/v) fetal bovine serum (Clonetics).

Test Compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10× Growth Factors: Solutions of human VEGF$_{165}$ (500 ng/mL; R&D Systems) and bFGF (10 ng/mL; R&D Systems) are prepared in Assay Medium.

10× [$^3$H]Thymidine: [Methyl-$^3$H]thymidine (20 Ci/mmol; Dupont-NEN) is diluted to 80 μCi/mL in low-glucose DMEM.

Cell Wash Medium: Hank's balanced salt solution (Mediatech) containing 1 mg/mL bovine serum albumin (Boehringer-Mannheim).

Cell Lysis Solution: 1 N NaOH, 2% (w/v) Na$_2$CO$_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% CO$_2$.

2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% CO$_2$ for 2 hours to allow test compounds to enter cells.

3. After the 2-hour pretreatment period, cells are stimulated by addition of 10 μL/well of either Assay Medium, 10×VEGF solution or 10×bFGF solution. Cells are then incubated at 37° C. and 5% CO$_2$.

4. After 24 hours in the presence of growth factors, 10× [$^3$H]thymidine (10 μL/well) is added.

5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of Formula I are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 0.01–5.0 μM. These compounds may also show selectivity over related tyrosine kinases (e.g., FGFR1 and the Src family; for relationship between Src kinases and VEGFR kinases, see Eliceiri et al., Molecular Cell, Vol. 4, pp.915–924, December 1999).

III. FLT-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:

1. Inhibitors were diluted to account for the final dilution in the assay, 1:20.

2. The appropriate amount of reaction mix was prepared at room temperature:

10× Buffer (20 mM Tris pH 7.4/0.1 M NaCl/1 mM DTT final)

0.1M MnCl$_2$ (5 mM final)

pEY substrate (75 μg/mL)

ATP/[$^{33}$P]ATP (2.5 μM/1 μCi final)

BSA (500 μg/mL final).

3. 5 μL of the diluted inhibitor was added to the reaction mix. (Final volume of 5 μL in 50% DMSO). To the positive control wells, blank DMSO (50%) was added.

4. 35 μL of the reaction mix was added to each well of a 96 well plate.

5. Enzyme was diluted into enzyme dilution buffer (kept at 4° C.).

6. 10 μL of the diluted enzyme was added to each well and mix (5 nM final). To the negative control wells, 10 μL 0.5 M EDTA was added per well instead (final 100 mM).

7. Incubation was then carried out at room temperature for 30 minutes.

8. Stopped by the addition of an equal volume (50 μL) of 30% TCA/0.1M Na pyrophosphate.

9. Incubation was then carried out for 15 minutes to allow precipitation.

10. Transfered to Millipore filter plate.

11. Washed 3× with 15% TCA/0.1M Na pyrophosphate (125 μL per wash).

12. Allowed to dry under vacuum for 2–3 minutes.

13. Dryed in hood for ~20 minutes.

14. Assembled Wallac Millipore adapter and added 50 μL of scintillant to each well and counted.

As seen in Table I below, the compounds of the instant invention, as represented by 4-4, 5-6, and 10-6, show enhanced pharmacokinetic properties as compared to previously reported compounds in WO 01/17995 A1, for example.

TABLE I

Pharmacokinetic Data of Representative Compounds

| Compound | Dog | | | Rat | | | Rhesus Monkey | | |
|---|---|---|---|---|---|---|---|---|---|
| | t1/2 (h) | Cl (ml/min/kg) | Bio-availability | t1/2 (h) | Cl (ml/min/kg) | Bio-availability | t1/2 (h) | Cl (ml/min/kg) | Bio-availability |
| WO 01/17995 A1 | 2.1 | 2.6 | — | — | — | — | — | — | — |
| WO 01/17995 A1 | 3.4 | 3.6 | 49% | 1.6 | 15.5 | — | — | — | — |
| WO 01/17995 A1 | 1.4 | 14.0 | — | — | — | — | — | — | — |
| 4-4 | 17.4 | 0.5 | 99% | 1.9 | 10.7 | 49% | 1.7 | 13.4 | 43% |
| 5-6 | 6.3 | 1.8 | 95% | 1.1 | 16.3 | 70% | 5.5 | 3.0 | 67% |
| 10-6 | 7.0 | 2.0 | 75% | 2.4 | 3.0 | 75% | — | — | — |

EXAMPLES

Examples provided are intended to assist in a further understanding of the invention. Particular materials employed, species and conditions are intended to be further illustrative of the invention and not limiting of the reasonable scope thereof. The compounds of this invention may be prepared by employing reactions as shown in the following schemes, in addition to other standard manipulations that are known in the literature.

SCHEME 1

Synthesis of 2-chloro-thiazole-5-carbonitrile (1-2)

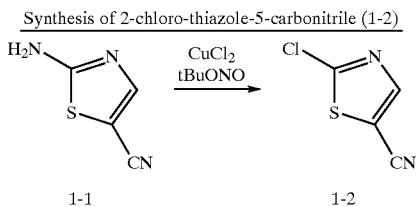

2-Chloro-thiazole-5-carbonitrile (1-2)

A flame dried round bottom flask under $N_2$ was charged with 150 mL anhydrous MeCN. $CuCl_2$ (12.9 g, 95.9 mmol, 1.2 equiv) was added and the reaction was maintained in a room temperature bath. tert-Butylnitrite (14.3 mL, 120 mmol, 1.5 equiv) was added gradually over 10 minutes. After 10 minutes, 2-amino-thiazole-5-carbonitrile (1-1, 10.0 g, 79.9 mmol) was added as a solid gradually. The reaction was stirred at room temperature for 4 hours. The reaction was poured into 400 mL 0.5M HCl (aq). The mixture was extracted 3× with EtOAc. The organic phases were dried over $Na_2SO_4$, filtered and concentrated to afford pure desired product.

$^1$H NMR (CDCl$_3$) δ 8.04 (s).

SCHEME 2

Synthesis of 4-(t-butyl-dimethyl-silanyloxymethyl)-pyridin-2-ylamine (2-5)

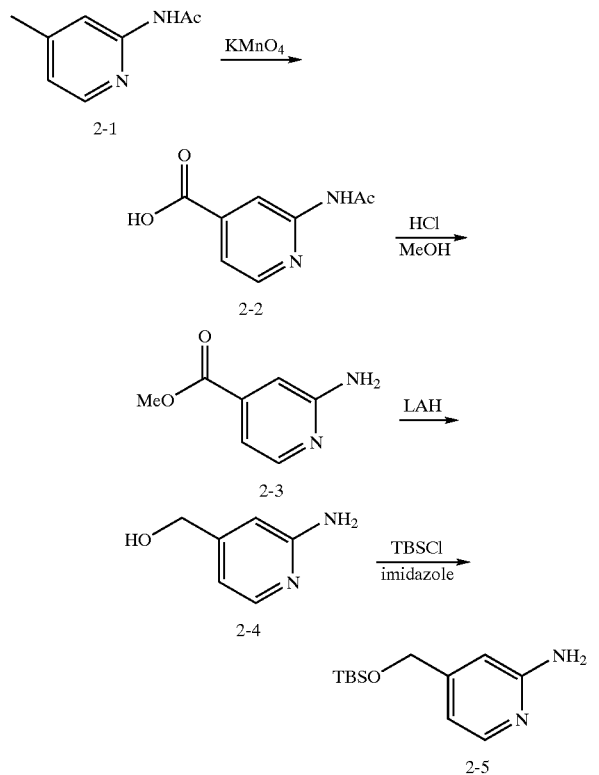

2-Acetylamino-isonicotinic acid (2-2)

N-(4-Methyl-pyridin-2-yl)-acetamide, 70 g (466 mmol) was stirred in 400 mL water. The mixture was warmed to 80° C. $KMnO_4$ (368 g, 2.33 mol, 5 equiv) was added dissolved in water over 45 minutes. The solution was heated to reflux for 3 hours. The reaction was then cooled and filtered. The filtrate was concentrated in vacuo to afford the desired product. $^1$H NMR (CD$_3$OD) δ 8.62 (s, H), 8.42 (d, 1H, J=5.1 Hz), 7.59 (dd, 1H, J=5.1 Hz), 2.19 (s, 3H).

2-Amino-isonicotinic acid methyl ester (2-3)

2-Acetylamino-isonicotinic acid (3.10 g, 17.2 mmol) was stirred in 35 mL MeOH at 0° C. HCl (g) was bubbled through the solution for 10 minutes and then the reaction was heated to reflux. After 16 hours the reaction was concentrated in vacuo. The residue was diluted with water and the pH was adjusted to 7 with $Na_2CO_3$ (s). A white precipitate formed which was filtered to afford a portion of pure desired product. The aqueous phase was extracted three times with 95:5 dichloromethane (DCM)/nBuOH. The organic phases were dried over $Na_2SO_4$, filtered and concentrated to afford more of the pure product as a white solid. $^1$H NMR (CDCl$_3$) δ 8.19 (d, 1H, J=5.3 Hz), 7.17 (dd, 1H, J=1.4, 5.3 Hz), 7.07 (d, 1H, J=1.3 Hz), 4.64 (bs, 2H), 3.92 (s, 3H). MS [M+H]+=153.0.

(2-Amino-pyridin-4-yl)-methanol (2-4)

2-Amino-isonicotinic acid methyl ester (6.0 g, 39.4 mmol) was dissolved in 80 mL anhydrous THF in a flame dried round bottom flask under nitrogen gas. The solution was cooled to −45° C. and LAH (39.4 mL, 1M in THF) was added slowly. The reaction was allowed to warm to 0° C. and was quenched by the addition of 15 mL of 1M NaOH (aq). The solution was filtered and the solid was washed with THF. The filtrate was concentrated to afford the pure product.

$^1$H NMR (DMSO-d$_6$) δ 7.79 (d, 1H, J=5.2 Hz), 6.41 (s, 1H), 6.38 (d, 1H, J=5.9 Hz), 5.79 (bs, 2H), 5.19 (t, 2H, J=5.7), 4.35 (d, 2H, J=5.6 Hz).

4-(tert-Butyl-dimethyl-silanyloxymethyl)-pyridin-2-ylamine (2-5)

(2-Amino-pyridin-4-yl)-methanol (4.68 g, 37.7 mmol) was dissolved in 40 mL anhydrous DMF under $N_2$. Imidazole (2.57 g, 37.7 mmol, 1 equiv) was added followed by the addition of TBSCl (5.68 g, 37.7 mmol, 1 equiv). After 2 hours the reaction was quenched by the addition of water. A precipitate formed which was filtered to afford pure desired product. The aqueous filtrate was extract 3× with EtOAc. The organic phases were dried over $Na_2SO_4$, filtered and concentrated to afford additional impure material. $^1$H NMR (CDCl$_3$) δ 7.99 (d, 1H, J=5.8 Hz), 6.57 (d, 1H, J=5.1 Hz), 6.51 (s, 1H), 4.64 (s, 2H), 4.40 (bs, 2H), 0.95 (s, 9H), 0.11 (s, 6H).

SCHEME 3

Synthesis of 2-(4-chloromethyl-pyridin-2-ylamino)-thiazole-5-carbonitrile (3-3)

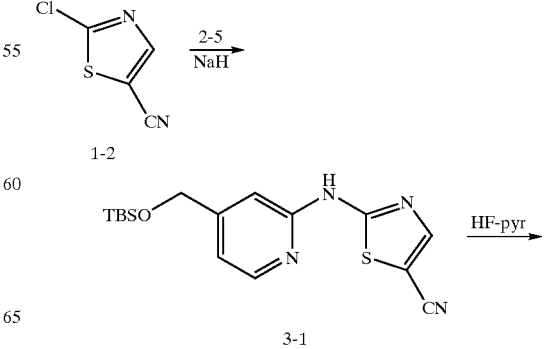

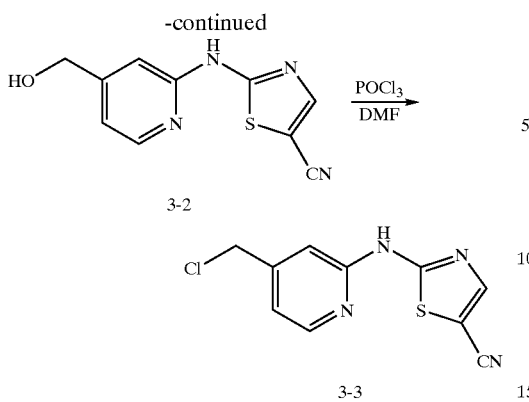

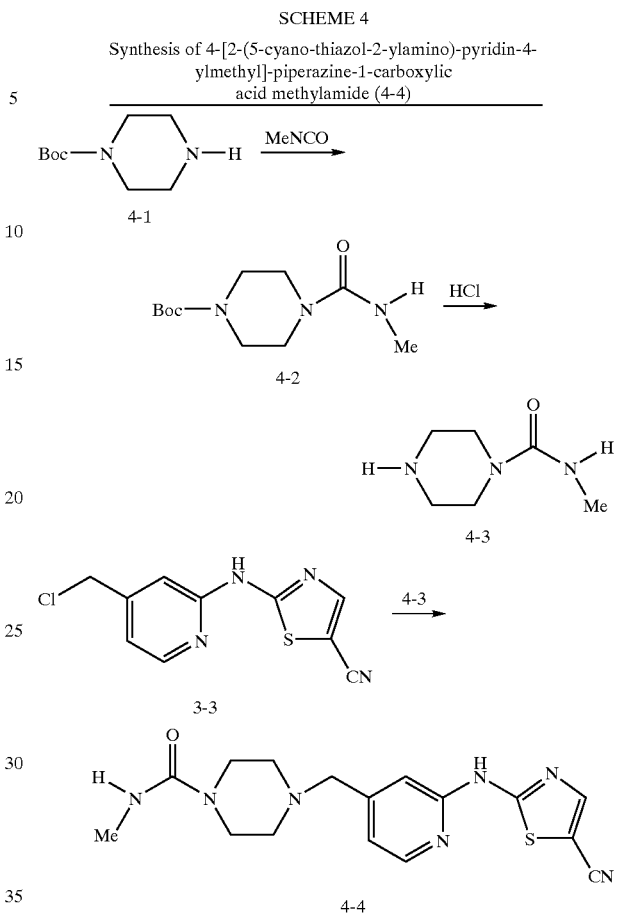

SCHEME 4

Synthesis of 4-[2-(5-cyano-thiazol-2-ylamino)-pyridin-4-ylmethyl]-piperazine-1-carboxylic acid methylamide (4-4)

2-[4-(tert-Butyl-dimethyl-silanyloxymethyl)-pyridin-2-ylamino]-thiazole-5-carbonitrile (3-1)

4-(tert-Butyl-dimethyl-silanyloxymethyl)-pyridin-2-ylamine (2-5, 5.94 g, 24.9 mmol) was dissolved in 50 mL anhydrous tetrahydrofuran (THF) under $N_2$. NaH (60% suspension, 2.99 g, 74.8 mmol, 3 equiv) was added (vigorous bubbling occured) and the resulting mixture was stirred for 15 minutes. 2-Chloro-thiazole-5-carbonitrile (1-2, 4.32 g, 29.9 mmol) was added and the reaction was heated to reflux. After 2 hours the reaction was cooled and was quenched by the addition of water. The THF was removed in vacuo and the resulting aqueous solution was adjusted to pH=7 by the addition of 1M HCl (aq). The resulting precipitate was filtered and washed with water to provide reasonably pure product.

$^1$H NMR (CDCl$_3$) δ 10.32 (bs, 1H), 8.33 (d, 1H, J=5.3 Hz), 7.99 (s, 1H), 6.96 (s, 1H), 6.91 (d, 1H, J=5.3 Hz), 4.78 (s, 2H), 0.98 (s, 9H), 0.16 (s, 6H).

2-(4-Hydroxymethyl-pyridin-2-ylamino)-thiazole-5-carbonitrile (3-2)

2-[4-(tert-Butyl-dimethyl-silanyloxymethyl)-pyridin-2-ylamino]-thiazole-5-carbonitrile (1.30 g, 3.75 mmol) was dissolved in 10 mL anh THF. Hydrogen-fluoride (Aldrich, 5.0 mL) was added and the reaction was stirred for 20 minutes. The bulk of the solvent was removed in vacuo and the resulting residue was diluted with half-saturated NaHCO$_3$ (aq). A precipitate formed which was filtered and washed with water to afford the titled compound.

$^1$H NMR (DMSO-d$_6$) δ 12.23 (bs, 1H), 8.30 (d, 1H, J=5.3 Hz), 8.26 (s, 1H), 7.15 (s, 1H), 6.99 (d, 1H, J=5.3 Hz), 5.49 (t, 1H, J=5.7 Hz) 4.54 (d, 2H, J=5.7 Hz).

2-(4-Chloromethyl-pyridin-2-ylamino)-thiazole-5-carbonitrile (3-3)

2-(4-Hydroxymethyl-pyridin-2-ylamino)-thiazole-5-carbonitrile (0.883 g, 3.80 mmol) was stirred in anhydrous CH$_2$Cl$_2$ (12 mL) under N$_2$. Dimethylformamide (0.354 mL, 3.80 mmol, 1 equiv) was added followed by the addition of phosphorous oxychloride (0.294 mL, 3.80 mmol). After 4 hours the reaction was concentrated and quenched by the addition of saturated NaHCO$_3$ (aq). A precipitate formed which was filtered and washed with water to provide the titled compound.

$^1$H NMR (DMSO-d$_6$) δ 12.35 (bs, 1H), 8.40 (d, 1H, J=5.3 Hz), 8.28 (s, 1H), 7.20 (s, 1H), 7.12 (d, 1H, J=5.3 Hz), 4.82 (s, 2H).

To a solution of Boc-piperazine, 4-1, in CH$_2$Cl$_2$ (200 mL) was added 6.74 g (1 equiv) methylisocyanate in CH$_2$Cl$_2$ (50 mL). The reaction mixture was stirred at room temperature for 6 hours and another 0.25 eq (1.69 g) of methylisocyanate was added. The reaction mixture was then stirred at room temperature overnight. The reaction was subsequently quenched with water (75 mL) and extracted with CH$_2$Cl$_2$ (3×50 mL). The combined organics were dried over Na$_2$SO$_4$, filtered, and concentrated to afford 4-2 as a white solid. $^1$H NMR (CDCl$_3$) δ 4.44 (bs, 1H), 3.48–3.33 (m, 8H), 2.82 (d, 3H, J=4.58), 1.47 (s, 9H).

To a solution of 4-2 in CH$_2$Cl$_2$ at 0° C. was added excess 4.0M HCl (101.5 mL, 406 mmol, 3.5 equiv) in dioxane. The reaction mixture was allowed to warm to room temperature and was stirred for 4 hours. The mixture was then concentrated to afford 1-[(methylamino)carbonyl]piperazin-4-ium chloride, the HCl salt of 4-3, as an off white solid. $^1$H NMR (DMSO-d$_6$) δ 9.28 (bs, 1H), 7.94 (bs, 1H), 3.52 (m, 4H), 3.01 (m, 4H), 2.57 (s, 3H).

2-(4-Chloromethyl-pyridin-2-ylamino)-thiazole-5-carbonitrile 3-3 (8.00 g, 31.9 mmol) was stirred in 60 mL DMSO. 1-[(Methylamino)carbonyl]piperazin-4-ium chloride (11.5 g, 63.8 mmol) was added, followed by addition of triethylamine (13.34 mL, 95.7 mmol). The reaction was allowed to stir at room temperature for 15 hours, at which time an additional 2.00 g piperazine hydrochloride (11.1 mmol) was added. No further progress was observed so the reaction was warmed to 45° C. but there was still no further progress. The reaction was cooled to room temperature. An additional 6.6 mL Et$_3$N (48 mmol) was then added. After an additional hour, the reaction was diluted with 300 mL water.

The resulting precipitate was filtered, washed with water and air dried. The solid was purified by flash chromatography (eluted with 92:8 DCM/MeOH) to afford the product 4-4. $^1$H NMR (DMSO-d$_6$) δ 12.20 (bs, 1H), 8.32 (d, 1H, J=5.49 Hz), 8.26 (s, 1H), 7.13 (s, 1H), 7.03 (d, 1H, J=5.19 Hz), 6.42 (bd, 1H, J=4.27 Hz), 3.52 (s, 2H), 3.29 (m, 4H), 2.51 (d, 3H, J=4.27 Hz), 2.33 (m, 4H). [M+H]+=358.1443.

SCHEME 5

Synthesis of 2-[(4-{[4-(methylsulfonyl)piperidin-1-yl]methyl}pyridin-2-yl)amino]-1,3-thiazole-5-carbonitrile (5-6)

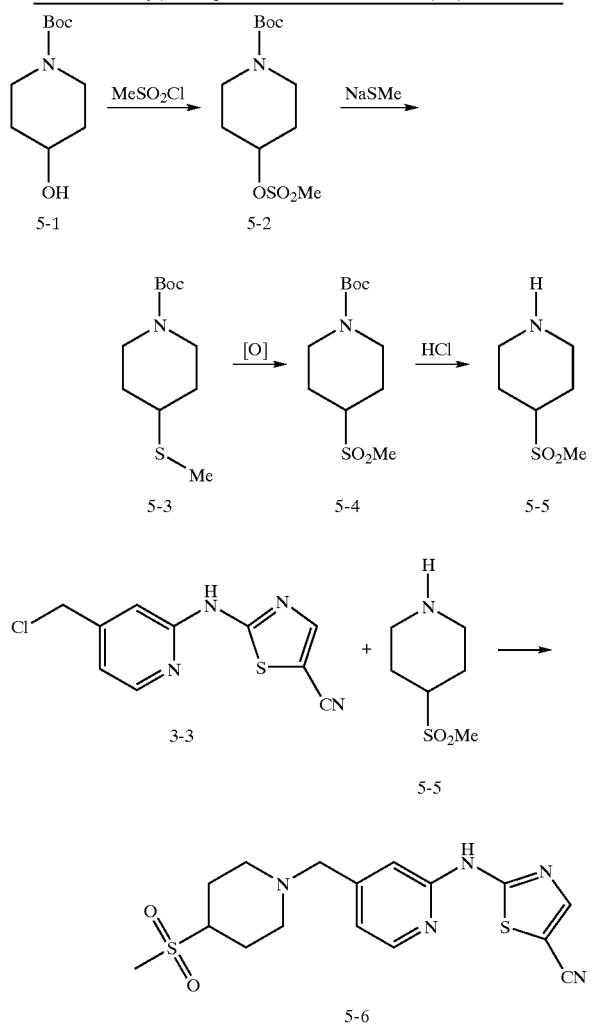

tert-Butyl 4-hydroxypiperidine-1-carboxylate 5-1 (21.650 g, 107.57 mmol) was dissolved in 200 mL CH$_2$Cl$_2$. N,N,N-Triethylamine (17.991 mL, 129.08 mmol) was added and the solution was cooled to 0° C. A solution of methanesulfonyl chloride (9.991 mL, 129.08 mmol) in 50 mL CH$_2$Cl$_2$ was then added dropwise. The solution was allowed to warm to room temperature. After 3.5 hours, 100 mL H$_2$O was added and the solution was stirred for 0.5 hour. The organic layer was separated, washed with 0.5N HCl and saturated NaHCO$_3$ (aq), dried (Na$_2$SO$_4$), filtered, and concentrated to afford tert-butyl 4-[(methylsulfonyl)oxy]piperidine-1-carboxylate 5-2 as an off white solid. $^1$H NMR (CDCl$_3$) δ 4.89 (m, 1H), 3.75–3.67 (m, 2H), 3.35–3.26 (m, 2H), 3.04 (s, 3H), 2.05–1.94 (m, 2H), 1.87–1.79 (m, 2H), 1.46 (s, 9H).

tert-Butyl 4-[(methylsulfonyl)oxy]piperidine-1-carboxylate 5-2 (27.060 g, 96.87 mmol) was dissolved in 150 mL DMF (dimethylformamide). Sodium thiomethoxide (13.579 g, 193.73 mmol) was added and the solution was heated to 80° C. for 17 hours. The solution was allowed to cool to room temperture. The reaction was then poured into 200 mL H$_2$O and was extracted with ether (4×). The combined organic layers were dried (Na$_2$SO$_4$), filtered, and concentrated to afford tert-butyl 4-(methylthio)piperidine-1-carboxylate 5-3 as a yellow oil. $^1$H NMR (CDCl$_3$) δ 4.01 (bs, 2H), 3.92 (m, 1H), 3.49 (m, 1H), 2.89 (m, 2H), 2.67 (m, 1H), 2.10 (s, 3H), 1.95–1.89 (m, 2H), 1.46 (s, 9H).

tert-Butyl 4-(methylthio)piperidine-1-carboxylate 5-3 (13.986 g, 60.45 mmol) was dissolved in 120 mL MeOH and the solution was cooled to 0° C. A mixture of oxone (74.329 g, 120.90 mmol) in 75 mL H$_2$O was slowly added. The mixture was stirred at 0° C. for 4 hours. 100 mL H$_2$O was then added and the precipitate was extracted with EtOAc (4×). The combined organic layers were dried (Na$_2$SO$_4$), filtered, and concentrated to afford tert-butyl 4-(methylsulfonyl) piperidine-1-carboxylate 5-4 as a white solid. $^1$H NMR (CDCl$_3$) δ 4.31 (bs, 2H), 2.96 (m, 1H), 2.85 (s, 3H), 2.76 (m, 2H), 2.13 (bd, 2H, J=13.43 Hz), 1.81–1.62 (m, 2H), 1.47 (s, 9H).

tert-Butyl 4-(methylsulfonyl)piperidine-1-carboxylate 5-4 (12.270 g, 46.59 mmol) was dissolved in 80 mL EtOAc and the solution was cooled to 0° C. 4.0M HCl in dioxane (58.240 mL, 232.95 mmol) was added and the solution was allowed to warm to room temperature. After 5 hours the reaction was concentrated in vacuo to afford 4-(methylsulfonyl)piperidine 5-5 as a white solid. HCl salt: $^1$H NMR (DMSO-d$_6$) δ 3.45–3.32 (m, 3H), 2.99 (s, 3H), 2.91 (bs, 2H), 2.16 (bd, 2H, J=13.12 Hz), 1.91–1.75 (m, 2H).

2-{[4-(Chloromethyl)pyridin-2-yl]amino}-1,3-thiazole-5-carbonitrile 3-3 (3.490 g, 13.92 mmol) was dissolved in 20 mL DMSO (dimethylsulfoxide). 4-(Methylsulfonyl) piperidine 5-5 (3.409 g, 20.88 mmol) and N-ethyl-N,N-diisopropylamine (9.70 mL, 55.68 mmol) were added and the solution was stirred for 17 hours. The reaction was diluted with water and the resulting precipitate was filtered and washed with water. The precipitate was then purified by flash column chromatography (gradient, 3–10% MeOH/CH$_2$Cl$_2$). The fractions containing the desired compound were concentrated to dryness to afford the titled compound 5-6 as the free base. $^1$H NMR (DMSO-d$_6$) δ 12.18 (bs, 1H), 8.32 (d, 1H, J=5.19 Hz), 8.26 (s, 1H), 7.15 (s, 1H), 7.01 (d, 1H, J=5.19 Hz), 3.54 (s, 2H), 3.14–3.09 (m, 1H), 2.93 (s overlapping m, 5H), 2.08–1.98 (m, 4H), 1.68–1.55 (m, 2H). [M+H]+=378.1057.

SCHEME 6

Synthesis of N-[(3R)-1-({2-[(5-cyano-1,3-thiazol-2-yl)amino]pyridin-4-yl}methyl)pyrrolidin-3-yl]-N'-methylurea (6-5)

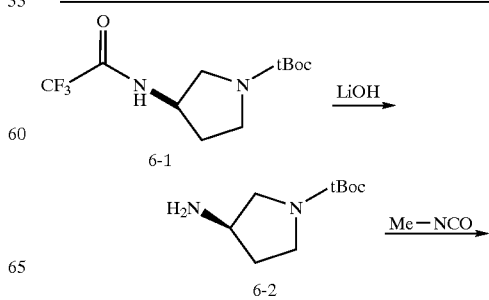

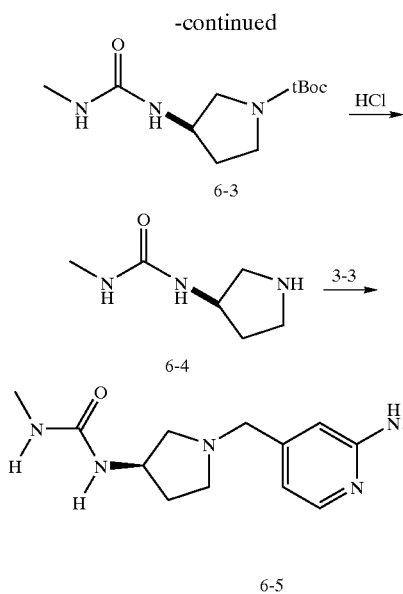

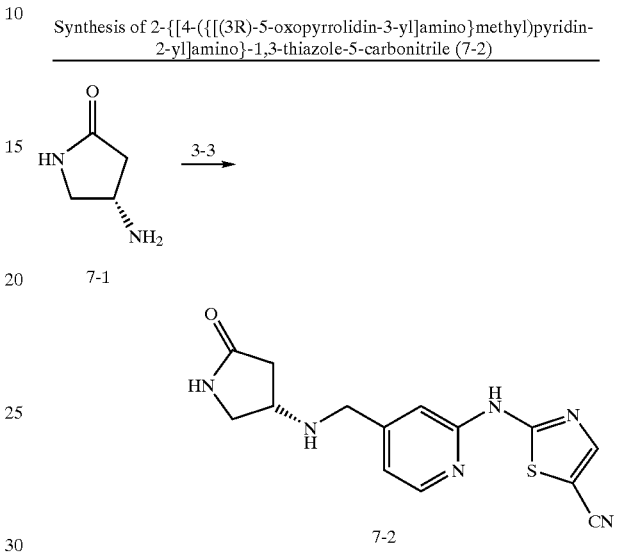

SCHEME 7

Synthesis of 2-{[4-({[(3R)-5-oxopyrrolidin-3-yl]amino}methyl)pyridin-2-yl]amino}-1,3-thiazole-5-carbonitrile (7-2)

tert-Butyl-(3R)-3-[(trifluoroacetyl)amino]pyrrolidine-1-carboxylate 6-1 (6.30 g, 22.32 mmol) was dissolved in 80 mL of 4:1 THF: H₂O. Lithium hydroxide hydrate (1.873 g, 44.64 mmol) was added and the reaction was stirred at room temperature. After 24 hours more lithium hydroxide hydrate (2.810 g, 66.96 mmol) was added. After 30 hours the solution was concentrated in vacuo (to remove THF) then extracted with EtOAc (3×). The combined organic layers were dried (Na₂SO₄), filtered, and concentrated to afford tert-butyl (3R)-3-aminopyrrolidine-1-carboxylate 6-2 as a yellow oil. Free base: ¹H NMR (DMSO-d₆) δ 3.45–3.14 (m, 4H), 2.88–2.83 (m, 1H), 1.92–1.77 (m, 1H), 1.61 (s, 2H), 1.56–1.46 (m, 1H), 1.39 (s, 9H).

tert-Butyl (3R)-3-aminopyrrolidine-1-carboxylate 6-2 (1.813 g, 9.73 mmol) was dissolved in 10 mL CH₂Cl₂. A solution of methylisocyanate (0.555 g, 9.73 mmol) in 10 mL CH₂Cl₂ was added. The solution was stirred for 3.5 hours. 50 mL H₂O was added and the precipitate was extracted with CH₂Cl₂ (2×). The combined organic layers were dried (Na₂SO₄), filtered, and concentrated to afford tert-butyl (3R)-3-{[(methylamino)carbonyl]amino}pyrrolidine-1-carboxylate 6-3 as a white semi-solid. Free base: ¹H NMR (DMSO-d₆) δ 6.15 (bs, 1H), 5.63 (bd, 1H, J=4.22 Hz), 4.02 (m, 1H), 3.42–3.34 (m, 1H), 3.28–3.19 (m, 2H), 2.93–2.98 (m, 1H), 2.53 (d, 3H, J=4.58 Hz), 1.99–1.93 (m, 1H), 1.68–1.63 (m, 1H), 1.39 (s, 9H).

tert-Butyl-(3R)-3-{[(methylamino)carbonyl]amino}pyrrolidine-1-carboxylate 6-3 (2.174 g, 8.93 mmol) was dissolved in 3 mL CH₂Cl₂ and the solution was cooled to 0° C. 4.0M HCl in dioxane (33.50 mL, 134.0 mmol) was added and the solution was allowed to warm to room temperature. After 4.5 hours the reaction was concentrated in vacuo to afford N-methyl-N'-[(3R)-pyrrolidin-3-yl]urea 6-4 as an off-white solid. HCl salt: ¹H NMR (DMSO-d₆) δ 9.13 (bs, 2H), 4.15 (m, 1H), 3.10–3.3.29 (m, 3H), 2.96–2.87 (m, 1H), 2.54 (s, 3H), 2.13–2.01 (m, 1H), 1.75 (m, 1H).

2-{[4-(Chloromethyl)pyridin-2-yl]amino}-1,3-thiazole-5-carbonitrile 3-3 (0.158 g, 0.63 mmol) was dissolved in 1.5 mL DMSO. (3R)-N-[(Methylamino)carbonyl]pyrrolidin-3-aminium chloride (0.273 g, 1.26 mmol) and N-ethyl-N,N-diisopropylamine (0.440 mL, 2.53 mmol) were added and the solution was stirred for 28 hours. The solution was purified by reverse phase chromatography (gradient, 5–100% CH₃CN/H₂O+0.1% TFA). The fractions containing the desired compound were concentrated to dryness to afford the TFA salt of 6-5. TFA salt: ¹H NMR (CD₃OD) δ 8.51 (bd, 1H, J=5.9 Hz), 8.05 (s, 1H), 7.16 (s, 2H), 4.51–4.42 (m, 2H), 4.39–4.26 (m, 1H), 3.98 (s, 2H), 3.76 (bs, 1H), 3.45 (bs, 1H), 2.68 (s, 3H), 2.57 (bs, 1H), 2.06 (bs, 1H). [M+H]+= 358.1456.

2-{[4-(Chloromethyl)pyridin-2-yl]amino}-1,3-thiazole-5-carbonitrile 3-3 (0.130 g, 0.52 mmol) was dissolved in 1 mL DMSO. (4S)-4-Aminopyrrolidin-2-one 7-1 (0.104 g, 1.04 mmol)—prepared according to WO-94/17090, hereby incorporated by reference—was added and the solution was stirred for 7 days. The solution was purified by reverse phase chromatography (gradient, 5–100% CH₃CN/H₂O+0.1% TFA). The fractions containing the desired compound were concentrated to dryness to afford the TFA salt of 7-2. TFA salt: ¹H NMR (DMSO-d₆) δ 12.52 (s, 1H), 9.34 (bs, 2H), 8.49 (d, 1H, J=5.12 Hz), 8.31 (s, 1H), 7.93 (s, 1H), 7.20 (s overlapping d, 3H), 4.26 (bs, 2H), 4.05 (bs, 1H), 3.61 (m, 1H), 3.42 (m, 1H), 2.63 (m, 1H), 2.44 (m, 1H). [M+H]+= 315.1032.

SCHEME 8

Synthesis of (2-chloro-3-methyl-pyridin-4-yl)-methanol (8-4)

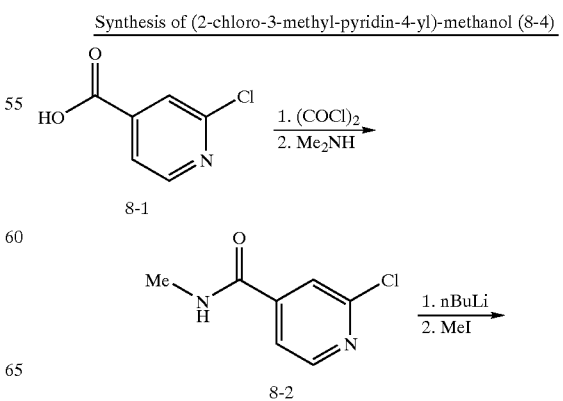

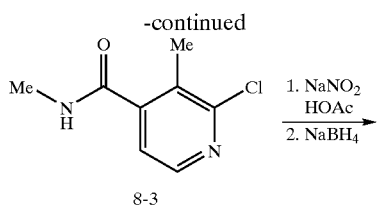

8-3

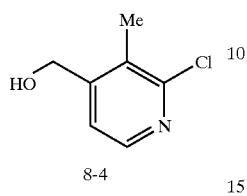

8-4

2-Chloro-N-methyl-isonicotinamide (8-2)

2-Chloro-isonicotinic acid (12-1, 5.15 g, 32.7 mmol) was stirred in 65 mL anhydrous THF under $N_2$. The reaction (not homogeneous) was cooled to 0° C. and oxalyl chloride (2.85 mL, 32.7 mmol) was added, followed by addition of 1 drop anhydrous DMF. Slight bubbling occurred. The reaction was allowed to warm to room temperature. After 4 hours reaction is homogeneous and after a total of 5 hours the reaction was quickly added by pipette to a solution of methylamine (7.11 g, 228 mmol) in EtOH (20 mL). The resulting solution was concentrated in vacuo and diluted with saturated $NaHCO_3$ (aq). The solution was extracted 3× with EtOAc and the organic extracts were dried over $Na_2SO_4$, filtered ands concentrated to provide the titled compound. $^1$H NMR ($CDCl_3$) δ 8.50 (d, 1H, J=5.1 Hz), 7.66 (s, 1H), 7.53 (d, 1H, J=5.1 Hz), 6.36 (bs, 1H), 3.04 (d, 2H, J=5.0 Hz).

2-Chloro-3,N-dimethyl-isonicotinamide (8-3)

2-Chloro-N-methyl-isonicotinamide (8-2, 1.03 g, 6.04 mmol) was dissolved in 12 mL anhydrous THF and the resulting solution was cooled to −78° C. nBuLi (1.6 M in hexane, 7.55 mL, 12.1 mmol) was added slowly. After 20 minutes MeI (0.375 mL, 6.04 mmol) was added slowly. Approximately halfway through the addition a brown gum quickly formed in the mixture. The remainder of the MeI was added and the reaction was allowed to warm to 0° C. and then to room temperature. After 30 minutes at room temperature the reaction was quenched with water. The mixture was extracted 3× with EtOAc, and the organic extracts were dried over $Na_2SO_4$, filtered, and concentrated. $^1$H NMR showed 2:1:1 monomethylated 8-3:dimethylated:starting material. Purification by flash column chromatography (98:2 DCM/MeOH) afforded a 2:1 mixture of the titled compound and 2-chloro-3,N-dimethyl-isonicotinamide.

(2-Chloro-3-methyl-pyridin-4-yl)-methanol (8-4)

2-Chloro-3,N-dimethyl-isonicotinamide (8-3, impure, 0.160 g) was stirred in 3 mL 2:1 $HOAc/Ac_2O$. The solution was cooled to 0° C. and $NaNO_2$ (0.120 g, 1.73 mmol) was added. After 30 minutes the reaction was allowed to warm to room temperature. After 6 hours an additional 60 mg (0.87 mmol) $NaNO_2$ was added, and the reaction was stirred overnight. The solution was diluted with saturated $NaHCO_3$ (aq), and extracted 3× w/EtOAc. The combined organic phases were dried over $Na_2SO_4$, filtered and concentrated. The residue was purified by flash column chromatography (4:1 hexane/ethylacetate, using a small amount of DCM to dissolve sample in mobile phase) to afford the nitroso amide, still as a 3:1 mixture with a by-product. A sample of this mixture (0.227 g) was dissolved in 4 mL THF. $NaBH_4$ (0.120 g, 3.17 mmol) was added and the resulting reaction was stirred at room temperature for 1 hour. The reaction was quenched with 1M HCl. The solution was then made basic with saturated $NaHCO_3$ (aq) and extracted 3× with EtOAc. The combined organic phases were dried over $Na_2SO_4$, filtered and concentrated to provide the titled compound as a colorless oil.

SCHEME 9

Synthesis of 4-[2-(5-cyano-thiazol-2-ylamino)-5-methyl-pyridin-4-yl]methyl]-piperzine-1-carboxylic acid methylamide (9-10)

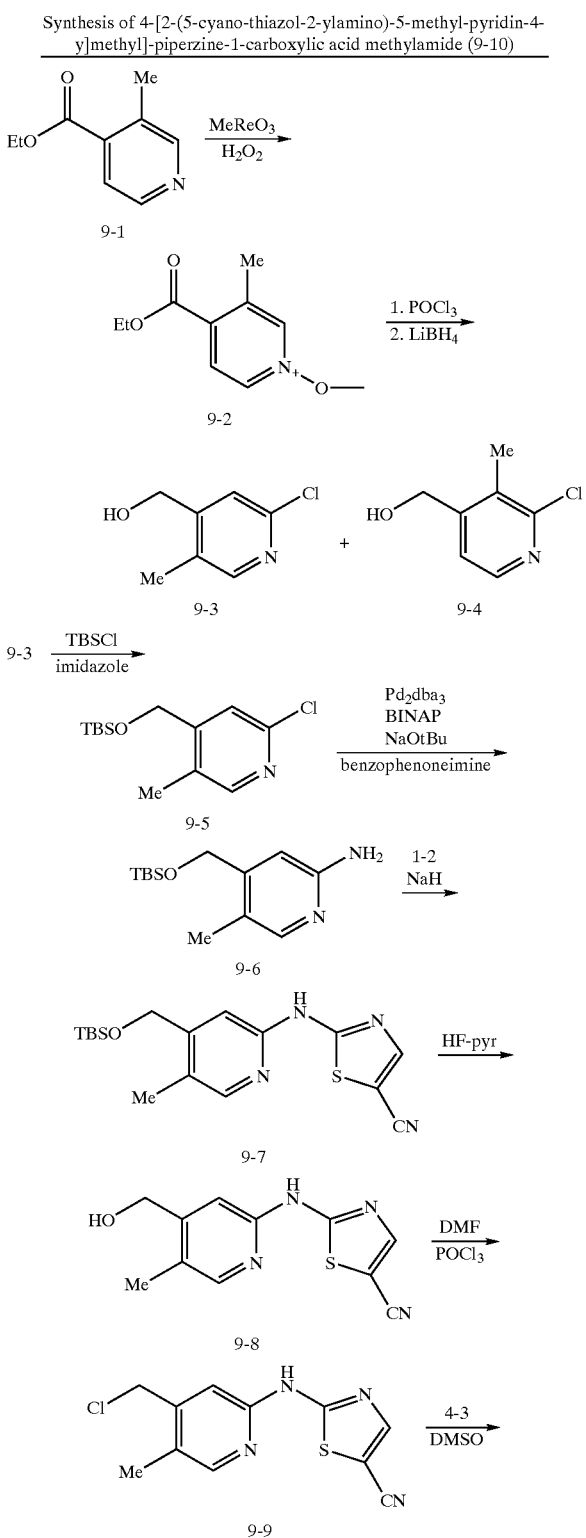

-continued

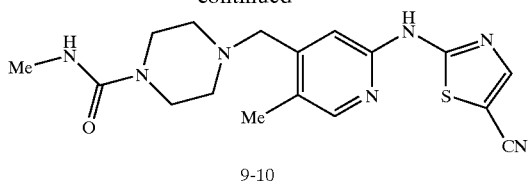

9-10

3-Methyl-1-oxy-isonicotinic acid ethyl ester (9-2)

3-Methyl-isonicotinic acid ethyl ester (K. Clarke, J. Goulding, R. M. Scrowston *J. Chem. Perkin Trans.* 1 1984, 1501–1505. 9-1, 1.48 g, 8.96 mmol) was dissolved in 3 mL of dichloromethane. Methyl trioxorhenium (11 mg, 0.040 mmol) was added followed by the addition of hydrogen peroxide (30% aqueous, 1.83 mL, 17.9 mmol). The reaction was allowed to stir overnight. After 20 hours, 20 mg of $MnO_2$ was added to the reaction (vigorous bubbling occurred). After bubbling had subsided (30 minutes) the reaction was diluted with water and extracted 3× with dichloromethane. The combined extracts were dried over $Na_2SO_4$, filtered and concentrated to afford 9-2. $^1H$ NMR ($CDCl_3$) δ 8.06 (s overlapping with d 2H), 7.82 (d, 1H), 4.37 (q, 2H, J=7.0 Hz), 2.55 (s, 3H), 1.40 (t, 3H, J=7.0 Hz).

(2-Chloro-5-methyl-pyridin-4-yl)-methanol (9-3) and (2-Chloro-3-methyl-pyridin-4-yl)-methanol (9-4)

3-Methyl-1-oxy-isonicotinic acid ethyl ester (9-2, 2.08 g, 11.5 mmol) was stirred in $POCl_3$ (10.7 mL, 17.6 g, 115 mmol) in a flask equipped with a reflux condenser and a drying tube. The resulting mixture was heated to reflux. After 2 hours the reaction was cooled to room temperature. The excess $POCl_3$ was removed in vacuo. The residue was diluted with dichloromethane and washed with aqueous $NaHCO_3$ (sat). The aqueous phase was extracted 2× with dichloromethane, dried over $Na_2SO_4$, filtered and concentrated. This afforded two isomeric products as a 2:1 mixture. This mixture was dissoved in 25 mL anhydrous THF in an oven dried flask under $N_2$. A reflux condenser was added and a solution of $LiBH_4$ in THF (2 M, 6.38 mL, 12.8 mmol) was added. The reaction was heated to reflux for 1 hour, allowed to cooled to room temperature, and was then quenched by the addition of 1 M HCl (aq). The solution was extracted 3× with dichloromethane. The combined extracts were dried over $Na_2SO_4$, filtered and concentrated. The resulting residue was purified by flash column chromatography (dissolved sample in DCM, eluted with 4:1 DCM/EA) which afforded good separation of the isomers. The first to elute was 9-3 as a white solid. $^1H$ NMR. $^1H$ NMR ($CDCl_3$) δ 8.06 (s, 1H), 7.43 (s, 1H), 4.70 (s, 2H), 2.20 (s, 3H), 1.95 (bs). The second to elute was 9-4, which was also a white solid. (9-4 can also be made as shown in Scheme 8.)

4-(tert-Butyl-dimethyl-silanyloxymethyl)-2-chloro-5-methyl-pyridine (9-5)

(2-Chloro-5-methyl-pyridin-4-yl)-methanol (9-3, 0.461 g, 2.93 mmol), tert-butyldimethylsilyl chloride (0.485 g, 3.22 mmol) and imidazole (0.239 g, 3.51) were dissolved in 3 mL anhydrous DMF in an oven dried flask under $N_2$. After 24 hours, the reaction was diluted with water (~25 mL) and stirred for 20 minutes. The resulting precipitate was filtered, washed with water and air dried to afford the titled product, 9-5. $^1H$ NMR ($CDCl_3$) δ 8.05 (s, 1H), 7.43 (s, 1H), 4.64 (s, 2H), 2.16 (s, 3H), 0.96 (s, 9H), 0.13 (s, 6H).

4-(tert-Butyl-dimethyl-silanyloxymethyl)-5-methyl-pyridin-2-ylamine (9-6)

An oven dried flask under $N_2$ was charged with 4-(tert-butyl-dimethyl-silanyloxymethyl)-2-chloro-5-methyl-pyridine (9-5, 0.600 g, 2.21 mmol), NaOtBu (0.297 g, 3.09 mmol), tris(dibenzylideneacetone)dipalladium (0) (0.040 g, 0.040 mmol), racemic-2,2'-bis(diphenylphosphino)-1,1'-binaphthyl (0.083 g, 0.13 mmol) and anhydrous toluene (10 mL). Benzophenone imine (0.444 mL, 2.65 mmol) was added and the reaction was heated to 80° C. After 3 hours the reaction was allowed to cool to room temperature and was diluted with 50 mL of diethyl ether. The resulting mixture was filtered through celite, washing with ether. The filtrate was concentrated, redissolved in 10 mL MeOH and hydroxylamine (50% aqueous, 0.405 mL, 6.62 mmol) was added. After stirring overnight, an additional 0.680 mL of hydroxylamine solution was added. After 8 hours the solution was concentrated in vacuo. The residue was purified by flash column chromatography (sample was loaded in DCM and eluted with a 1:1 Hex/EA to EA, ethylacetate, gradient) to afford the titled product, 9-6. $^1H$ NMR indicates that product is contaminated with BINAP dioxide.

$^1H$ NMR ($CDCl_3$) δ 7.76 (s, 1H), 6.63 (s, 1H), 4.60 (s, 2H), 4.28 (bs, 2H), 2.04 (s, 3H), 0.96 (s, 9H), 0.13 (s, 6H).

2-[4-(tert-Butyl-dimethyl-silanyloxymethyl)-5-methyl-pyridin-2-ylamino]-thiazole-5-carbonitrile (9-7)

An oven dried flask under $N_2$ was charged with NaH (60% dispersion, 185 mg, 4.63 mmol). 5 mL of anhydrous THF was added followed by addition of 4-(tert-butyl-dimethyl-silanyloxymethyl)-5-methyl-pyridin-2-ylamine (9-6, 0.487 g, 1.93 mmol) and 2-chloro-5-cyanothiazole (1-2, 0.391 g, 2.70 mmol). The resulting solution was heated to reflux. After 1 hour the reaction was allowed to cool to room temperature and was then diluted with water. The pH was adjusted to 7 with 1 M HCl. The resulting precipitate was filtered and washed with water to afford 9-7.

2-(4-Hydroxymethyl-5-methyl-pyridin-2-ylamino)-thiazole-5-carbonitrile (9-8)

2-[4-(tert-Butyl-dimethyl-silanyloxymethyl)-5-methyl-pyridin-2-ylamino]-thiazole-5-carbonitrile (9-7, 0.650 g, 1.80 mmol) was dissolved in 5 mL THF. HF-pyridine (Aldrich), 0.5 mL, was added and the reaction was stirred at room temperature. After 4 hours the reaction was diluted with water and the pH was adjuted to 7 with $K_2CO_3$ (s). The resulting precipitate was filtered and washed with water to afford 9-8 as an orange solid which was used in the next step without further purification. $^1H$ NMR ($DMSO-d_6$) δ 12.15 (s, 1H), 8.24 (s, 1H), 8.10 (s, 1H), 7.26 (s, 1H), 5.48 (bs, 1H), 4.52 (s, 2H), 2.13 (s, 3H).

2-(4-Chloromethyl-5-methyl-pyridin-2-ylamino)-thiazole-5-carbonitrile (9-9)

2-(4-Hydroxymethyl-5-methyl-pyridin-2-ylamino)-thiazole-5-carbonitrile (9-8, 0.400 g, 1.62 mmol) was stirred in 5 mL of anhydrous dichloromethane. N,N-Dimethylformamide (0.125 mL, 1.62 mmol) was added followed by the addition of phosphorous oxychloride (0.151 mL, 1.62 mmol). After 2 hours the reaction was concentrated in vacuo. Half-saturated $NaHCO_3$ (aq) was added and the resulting precipitate was filtered and washed with water. Air drying provided the titled product, 9-9 contaminated with BINAP oxide. $^1H$ NMR ($DMSO-d_6$) δ 8.24 (s, 1H), 8.22 (s, 1H), 7.17 (s, 1H), 4.80 (s, 2H), 2.28 (s, 3H).

4-[2-(5-Cyano-thiazol-2-ylamino)-5-methyl-pyridin-4-ylmethyl]-piperazine-1-carboxylic acid methylamide (9-10)

2-(4-Chloromethyl-5-methyl-pyridin-2-ylamino)-thiazole-5-carbonitrile (9-9, 0.204 g, 0.771 mmol) and 4-methylcarbamoyl-piperazin-1-ium chloride (4-3, 0.277 g, 1.54 mmol) were dissolved in 2 mL DMSO. Diisopropyl-ethyl amine (0.537 mL, 3.08 mmol) was added and the reaction was stirred for 3.5 hours. The reaction mixture was then directly loaded onto a reverse phase purification system to afford the titled compound, 9-10, as the TFA salt. $^1H$ NMR (CD$_3$OD) δ 8.35 (s, 1H), 8.02 (s, 1H), 7.16 (s, 1H), 4.25 (s, 2H), 3.37 (bs, 4H), 3.24 (bs, 4H), 2.73 (s, 3H), 2.39 (s, 3H). MS [M+H]+=372.1.

SCHEME 10

Synthesis of 4-[2-(5-Cyano-thiazol-2-ylamino)-3-methyl-pyridin-4-ylmethyl]-piperazine-1-carboxylic acid methylamide (10-6)

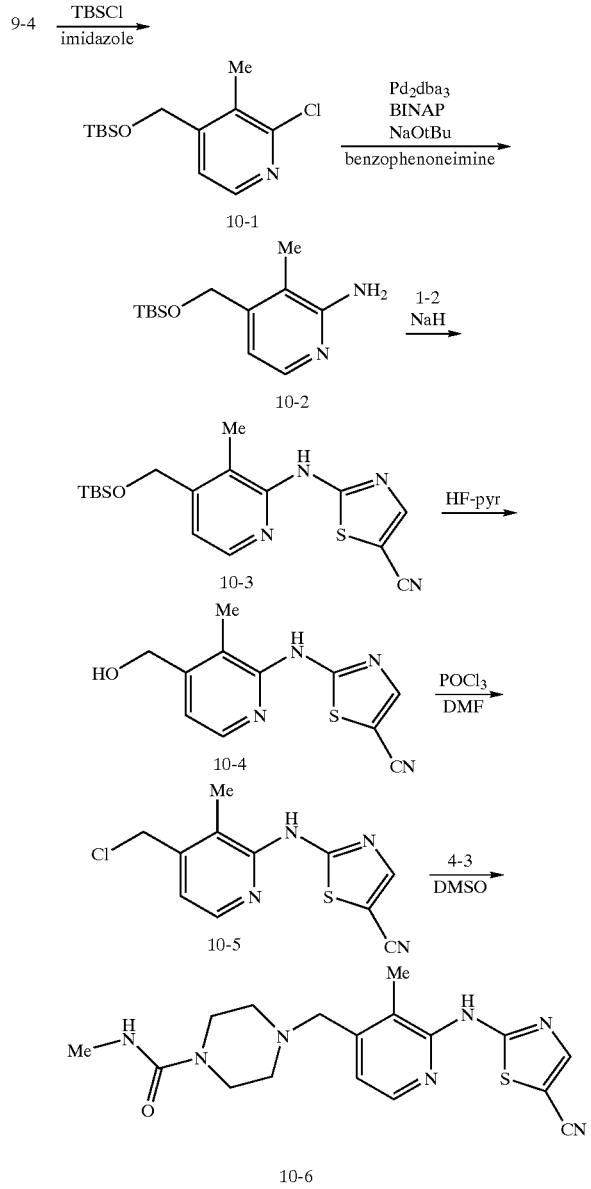

4-(tert-Butyl-dimethyl-silanyloxymethyl)-2-chloro-3-methyl-pyridine (10-1)

(2-Chloro-3-methyl-pyridin-4-yl)-methanol (9-4, 0.741 g, 4.70 mmol), tert-butyldimethylsilyl chloride (0.780 g, 5.17 mmol) and imidazole (0.384 g, 5.64) were dissolved in 5 mL anhydrous DMF in an oven dried flask under N$_2$. After 24 hours the reaction was diluted with water (~40 mL) and stirred for 20 minutes. The resulting precipitate was filtered, washed with water and air dried to afford the titled product. $^1$H NMR (CDCl$_3$) δ 8.23 (d, 1H, J=4.9 Hz), 7.40 (d, 1H, J=4.9 Hz), 4.69 (s, 2H), 2.27 (s, 3H), 0.96 (s, 9H), 0.13 (s, 6H).

4-(tert-Butyl-dimethyl-silanyloxymethyl)-3-methyl-pyridin-2-ylamine (10-2)

An oven dried flask under N$_2$ was charged with 4-(tert-butyl-dimethyl-silanyloxymethyl)-2-chloro-3-methyl-pyridine (10-1, 1.00 g, 3.68 mmol), NaOtBu (0.495 g, 5.15 mmol), tris(dibenzylideneacetone)dipalladium (0) (0.067 g, 0.070 mmol), racemic-2,2'-bis(diphenylphosphino)-1,1'-binaphthyl (0.137 g, 0.22 mmol) and anhydrous toluene (10 mL). Benzophenone imine (0.740 mL, 4.41 mmol) was added and the reaction was heated to 80° C. After 3 hours the reaction was allowed to cool to room temperature and was diluted with 50 mL of diethyl ether. The resulting mixture was filtered through celite, washing with ether. The filtrate was concentrated, redissolved in 10 mL MeOH and hydroxylamine (50% aqueous, 0.676 mL, 11.0 mmol) was added. After stirring overnight, an additional 0.680 mL of hydroxylamine solution was added. After 8 hours the solution was concentrated in vacuo. The residue was purified by flash column chromatography (sample was loaded in DCM and eluted with a DCM to 9:1 DCM/MeOH gradient) to afford the title product. $^1$H NMR indicates that product is contaminated with BINAP dioxide. $^1$H NMR (CDCl$_3$) δ 7.80 (d, 1H), 6.85 (d, 1H), 4.65 (s, 2H), 4.35 (bs, 2H), 2.00 (s, 3H), 0.95 (s, 9H), 0.15 (s, 6H).

2-[4-(tert-Butyl-dimethyl-silanyloxymethyl)-3-methyl-pyridin-2-ylamino]-thiazole-5-carbonitrile (10-3)

An oven dried flask under N$_2$ was charged with NaH (60% dispersion, 210 mg, 5.25 mmol). 5 mL of anhydrous THF was added followed by 4-(tert-butyl-dimethyl-silanyloxymethyl)-3-methyl-pyridin-2-ylamine (10-2, 0.602 g, 2.39 mmol) and 2-chloro-5-cyanothiazole (1-2, 0.414 g, 2.86 mmol). The resulting solution was heated to reflux. After 19 hours additional NaH (19 mg, 0.48 mmol) and 2-chloro-5-cyanothiazole (1-2, 0.069 g, 0.48 mmol) were added. After an additional 1 hour at reflux the reaction was allowed to cool to room temperature and diluted with water. The pH was adjusted to 7 with 1 M HCl. The resulting precipitate was filtered and washed with water to afford 10-3. $^1$H NMR (CDCl$^3$) δ 8.41 (bs, 1H), 8.27 (d, 1H, J=5.2 Hz), 7.94 (s, 1H), 7.19 (d, 1H, J=5.2 Hz), 4.74 (s, 2H), 2.21 (s, 3H), 0.96 (s, 9H), 0.13 (s, 6H).

2-(4-Hydroxymethyl-3-methyl-pyridin-2-ylamino)-thiazole-5-carbonitrile (10-4)

2-[4-(tert-Butyl-dimethyl-silanyloxymethyl)-3-methyl-pyridin-2-ylamino]-thiazole-5-carbonitrile (10-3, 0.920 g, 2.55 mmol) was dissolved in 5 mL THF. HF-pyridine (Aldrich), 0.5 mL, was added and the reaction was stirred at room temperature. After 4 hours an additional 0.5 mL of HF-pyridine was added and the reaction was allowed to stir overnight. After a total of 18 hours the reaction was diluted with water and the pH was adjusted to 7 with K$_2$CO$_3$ (s). The resulting precipitate was filtered and washed with water. Air drying afforded the crude product as an orange solid, which was used in the next step without further purification.

$^1$H NMR (DMSO-d$_6$) δ 11.40 (s, 1H), 8.30 (s, 1H), 8.26 (d, 1H, J=5.5 Hz), 7.21 (d, 1H, J=5.2 Hz), 4.56 (s, 2H), 2.24 (s, 3H). MS [M+H]+=247.1.

4-[2-(5-Cyano-thiazol-2-ylamino)-3-methyl-pyridin-4-ylmethyl]-piperazine-1-carboxylic acid methylamide (10-6)

2-(4-Hydroxymethyl-3-methyl-pyridin-2-ylamino)-thiazole-5-carbonitrile (10-4, 0.620 g, 2.52 mmol) was stirred in 5 mL of anhydrous dichloromethane. Anhydrous N,N-dimethylformamide (0.195 mL, 2.52 mmol) was added followed by phosphorous oxychloride (0.235 mL, 2.52 mmol). After 2 hours the reaction was quenched with half-saturated NaHCO$_3$ (aq). The aqueous phase was extracted 3× with DCM. The combined organic extracts were dried over Na₂SO₄, filtered and concentrated to afford an orange-brown solid. ¹H NMR indicated that this solid was composed of impure 2-(4-chloromethyl-3-methyl-pyridin-2-ylamino)thiazole-5-carbonitrile (10-5), containing BINAP dioxide impurity. This material and 4-methylcarbamoyl-piperazin-1-ium chloride (4-3, 0.445 g, 2.48 mmol) were dissolved in 3 mL DMSO. Diisopropyl-ethylamine (0.863 mL, 4.96 mmol) was added and the reaction was stirred for 5 hours. The reaction mixture was then directly loaded onto a reverse phase purification system, which afforded titled compound, 10-6, as the TFA salt. ¹H NMR (DMSO-d₆) δ 11.60 (s, 1H), 9.77 (bs, 1H), 8.36 (s overlapping with d, 2H), 7.23 (d, 1H, J=5.2 Hz), 6.69 (s, 1H), 4.44 (s, 2H), 4.03 (s, 2H), 3.36 (s, 2H), 3.06 (s, 4H), 2.59 (s, 3H), 2.42 (s, 3H). MS [M+H]+=372.2.

SCHEME 11

Synthesis of 4-({2-chloro-6-[(5-cyano-1,3-thiazol-2-yl)amino]pyridin-4-yl}methyl)-N-methylpiperazine-1-carboxamide (11-8)

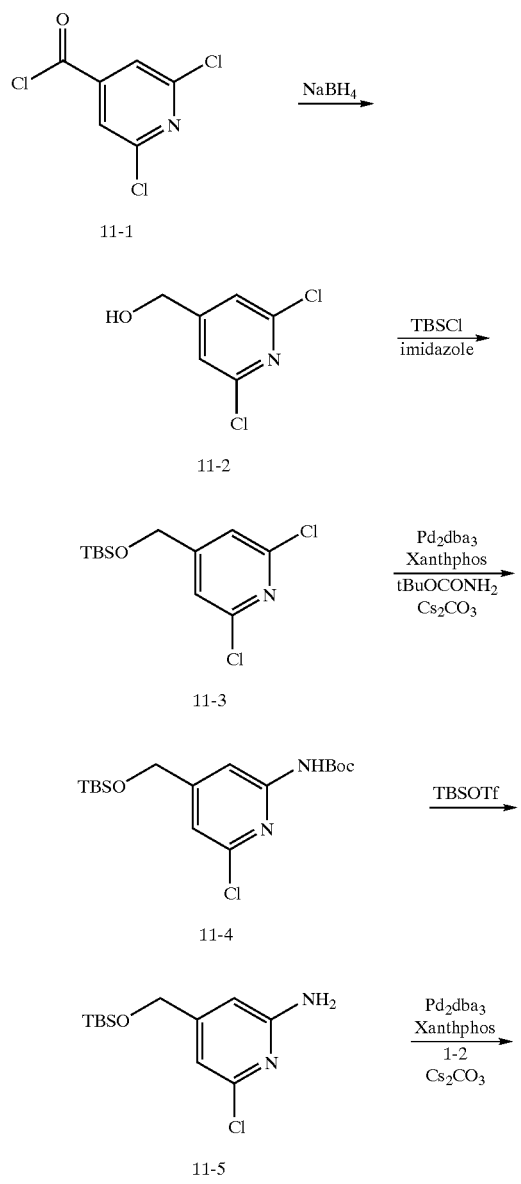

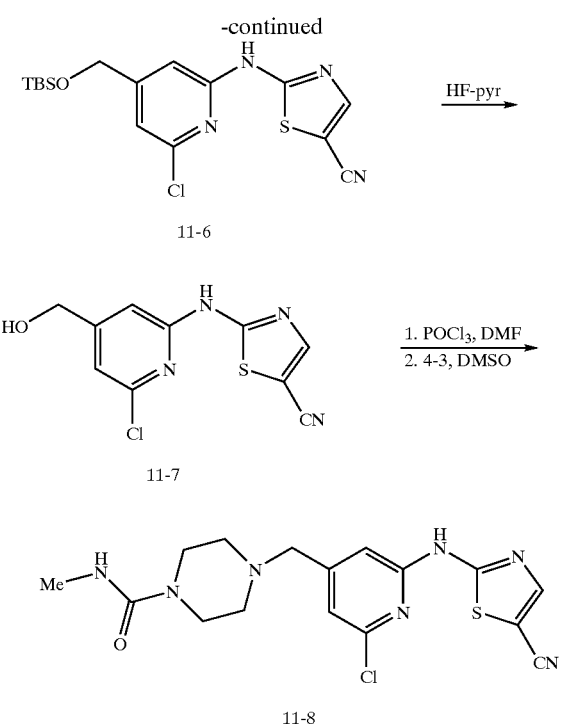

(2,6-Dichloro-pyridin-4-yl)-methanol (11-2)

2,6-Dichloro-isonicotinoyl chloride (11-1, 2.31 g, 11.0 mmol) was dissolved in 20 mL of anhydrous THF in an oven dried flask under N₂. The solution was cooled to 0° C. and LiBH₄ (2 M solution in THF, 3.29 mL, 6.59 mmol) was added dropwise. After 1 hour the reaction was quenched by the addition of 1M HCl. After 10 minutes the mixture was diluted with saturated NaHCO₃ (aq). The aqueous phase was extracted 3× with DCM. The combined organic phases were dried over Na₂SO₄, filtered and concentrated to afford 11-2 as a white solid. ¹H NMR (CDCl₃) δ 7.30 (s, 2H), 4.75 (d, 2H), 2.15 (t, 1H). MS [M+H]+=178.0.

4-(tert-Butyl-dimethyl-silanyloxymethyl)-2,6-dichloro-pyridine (11-3)

A flame dried flask under N₂ was charged with (2,6-dichloro-pyridin-4-yl)-methanol (11-2, 1.02 g, 5.73 mmol), imidazole (0.468 g, 6.88 mmol) and tert-butyldimethylsilyl chloride (0.950 g, 6.30 mmol). 6 mL of anhydrous DMSO were then added. After 30 minutes the reaction had become thick with a white precipitate. After an additional 1 hour the reaction was diluted with water (~40 mL). The resulting white precipitate was filtered, washed with water, and air dried to afford the titled product 11-3. ¹H NMR (CDCl₃) δ 7.22 (s, 2H), 4.71 (s, 2H), 0.95 (s, 9H), 0.12 (s, 6H).

tert-Butyl 4-({[tert-butyl(dimethyl)silyl]oxy}methyl)-6-chloropyridin-2-ylcarbamate (11-4)

An oven dried flask under N₂ was charged with 4-(tert-butyl-dimethyl-silanyloxymethyl)-2,6-dichloro-pyridine (11-3, 1.54 g, 5.27 mmol), t-butylcarbamate (0.741 g, 6.32 mmol), cesium carbonate (2.40 g, 7.38 mmol), tris(dibenzylideneacetone)dipalladium(0) (0.048 g, 0.050 mmol) and Xantphos (0.092 g, 0.030 mmol). Anhydrous dioxane, 10 mL, was added and the reaction was heated to reflux. After 24 hours the reaction was diluted with water and extracted 3× with DCM. The combined organic extracts were dried over Na₂SO₄, filtered and concentrated. Purification by flash column chromatography (eluted with a gradient from 65:35 Hex/DCM to 40:60) afforded the titled product, 11-4. ¹H NMR (CDCl₃) δ 7.62 (s, 1H), 7.12 (bs, 1H). 6.94 (s, 1H), 4.60 (s, 2H), 1.40 (s, 9H), 0.84 (s, 9H), 0.12 (s, 6H).

4-(tert-Butyl-dimethyl-silanyloxymethyl)-6-chloro-pyridin-2-ylamine (11-5)

[4-(tert-Butyl-dimethyl-silanyloxymethyl)-6-chloro-pyridin-2-yl]-carbamic acid tert-butyl ester (11-4, 0.885 g, 2.37 mmol) was dissolved in 5 mL DCM in a flame dried flask under $N_2$. The solution was cooled to 0° C. and tert-butyldimethylsilyl trifluoromethanesulfonate (1.09 mL, 4.75 mmol) was added. After 3 hours the reaction was warmed to room temperature and additional TBSOTf (0.545 mL, 2.37 mL) was added and the reaction was stirred overnight. Diisopropylethylamine (1.65 mL, 9.49 mmol) was added and after 10 minutes the reaction was quenched by the addition of saturated $NaHCO_3$ (aq). The aqueous phase was extracted 3× with DCM. The combined organic extracts were dried over $Na_2SO_4$, filtered and concentrated. Purification by flash column chromatography (9:1 hex/EA) afforded a primary product which was not the desired product. This residue was dissolved in ~25 mL MeOH and silica (~5 g) was added. Over the course of 3 days with stirring this primary product partially converted to desired 11-5. To the reaction was added 0.5 mL HOAc and the remaining material quickly converted. The silica was filtered off, washing with MeOH and the filtrates were concentrated in vacuo to afford the titled product, 11-5. $^1$H NMR ($CDCl_3$) δ 6.59 (s, 1H), 6.38 (s, 1H4.60 (s, 2H), 4.52 (bs, 2H), 0.94 (s, 9H), 0.11 (s, 6H).

2-[4-(tert-Butyl-dimethyl-silanyloxymethyl)-6-chloro-pyridin-2-ylamino]-thiazole-5-carbonitrile (11-6)

An oven dried flask under $N_2$ was charged with 4-(tert-butyl-dimethyl-silanyloxymethyl)-6-chloro-pyridin-2-ylamine (11-5, 0.488 g, 1.79 mmol), 2-chloro-5-cyanothiazole (1-2, 0.310 g, 2.15 mmol), cesium carbonate (0.816 g, 2.50 mmol), tris(dibenzylideneacetone)dipalladium (0) (0.033 g, 0.040 mmol) and Xantphos (0.062 g, 0.060 mmol). Anhydrous dioxane, 6 mL, was added and the reaction was heated to reflux. After 3 hours the reaction was cooled to room temperature and stirred overnight. The reaction was diluted with water and extracted 3× with DCM. The extracts were dried over $Na_2SO_4$, filtered and concentrated. The resulting solid was triturated with ether, and filtered to afford the product as a tan solid.

2-(6-Chloro-4-hydroxymethyl-pyridin-2-ylamino)-thiazole-5-carbonitrile (11-7).

2-[4-(tert-Butyl-dimethyl-silanyloxymethyl)-6-chloro-pyridin-2-ylamino]-thiazole-5-carbonitrile (11-6) was dissolved in 5 mL of THF. HF-pyr (Aldrich), 0.5 mL was added and the reaction was stirred at room temperature. After 1.5 hours the reaction was diluted with water and adjuted to pH 7 by the gradual addition of solid $K_2CO_3$. The mixture was extracted 3× with DCM. Large amounts of solid were suspended in the DCM extracts so the extracts were filtered and washed with DCM to afford the desired product, 11-7. $^1$H NMR (DMSO-$d_6$) δ 12.49 (s, 1H), 8.30 (s, 1H), 7.09 (s, 1H), 7.06 (s, 1H), 5.59 (t, 1H, J=5.8 Hz), 4.55 (d, 2H, J=5.5 Hz).

4-({2-Chloro-6-[(5-cyano-1,3-thiazol-2-yl)amino]pyridin-4-yl}methyl)-N-methylpiperazine-1-carboxamide (11-8)

2-{[6-Chloro-4-(hydroxymethyl)pyridin-2-yl]amino}-1,3-thiazole-5-carbonitrile 11-7 (0.132 g, 0.49 mmol) was stirred in anhydrous $CH_2Cl_2$ (2 mL) under $N_2$. N,N-Dimethylformamide (0.038 mL, 0.49 mmol) was added followed by the addition of phosphorous oxychloride (0.046 mL, 0.49 mmol). After 2.5 hours the reaction was concentrated and quenched by the addition of saturated $NaHCO_3$ (aq). A precipitate formed which was filtered and washed with water to afford 2-{[6-chloro-4-(chloromethyl)pyridin-2-yl]amino}-1,3-thiazole-5-carbonitrile as a yellow solid.

$^1$H NMR (DMSO-$d_6$) δ 12.63 (bs, 1H), 8.34 (s, 1H), 7.24 (s, 1H), 7.17 (s, 1H), 4.82 (s, 2H).

2-{[6-Chloro-4-(chloromethyl)pyridin-2-yl]amino}-1,3-thiazole-5-carbonitrile (0.103 g, 0.36 mmol) was dissolved in 2 mL DMSO. 1-[(Methylamino)carbonyl]piperazin-4-ium chloride (4-3, 0.129 g, 0.72 mmol) and N-ethyl-N,N-diisopropylamine (0.251 mL, 1.44 mmol) were added and the solution was stirred for 24 hours. The reaction was diluted with water and the resulting precipitate was filtered and washed with water. The precipitate was purified by flash column chromatography (gradient, 5–10% MeOH/$CH_2Cl_2$). The fractions containing the desired compound were concentrated to dryness to afford 11-8. $^1$H NMR (DMSO-$d_6$) δ 12.46 (bs, 1H), 8.39 (s, 1H), 8.31 (s, 1H), 7.11 (s, 2H), 6.43 (bd, 1H, J=4.27 Hz), 3.53 (s, 2H), 3.30 (m, 4H), 2.55 (d, 3H, J=4.27 Hz), 2.34 (m, 4H). [M+H]+=392.1026.

SCHEME 12

Synthesis of 4-({2-[(5-cyano-1,3-thiazol-2-yl)amino]-6-ethylpyridin-4-yl}methyl)-N-methylpiperazine-1-carboxamide (12-4)

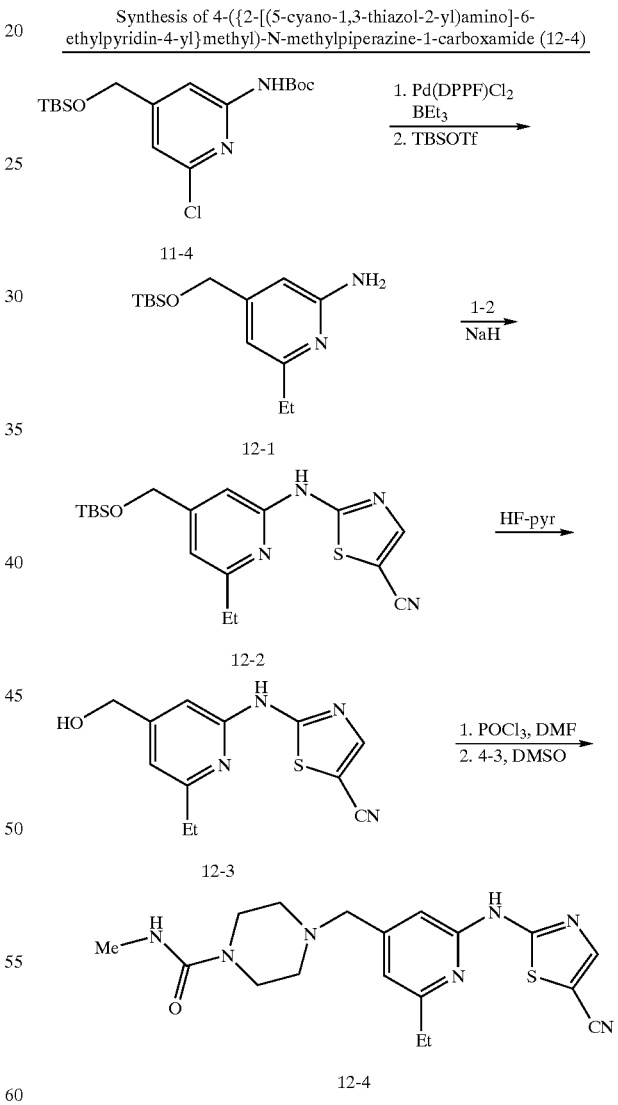

4-({[tert-butyl(dimethyl)silyl]oxy}methyl)-6-ethylpyridin-2-amine (12-1)

tert-Butyl 4-({[tert-butyl(dimethyl)silyl]oxy}methyl)-6-chloropyridin-2-ylcarbamate (11-4, 0.496 g, 1.33 mmol) was dissolved in 2 mL DMF. Dichloro[1,1'-bis(diphenylphosphino)ferrocene]palladium (II) dichloromethane adduct (0.087 g, 0.11 mmol), cesium carbonate (2.601 g, 7.98 mmol), and triethylborane (1M in hexanes) (3.190 mL, 3.19 mmol) were added and the solution was heated to 50° C. After 24 hours the reaction was allowed to cool to room temperature and was concentrated to afford a brown oil. The oil was filtered through celite and washed with $CH_2Cl_2$. The filtrate was concentrated to afford a light brown oil. The oil was purified by flash column chromatography (10:90 EtOAc/hexanes) to afford tert-butyl 4-({[tert-butyl(dimethyl)silyl]oxy}methyl)-6-ethylpyridin-2-ylcarbamate as a light yellow oil. Free base: $^1$H NMR ($CDCl_3$) δ 7.60 (s, 1H), 7.14 (bs, 1H), 6.91 (s, 1H), 4.71 (s, 2H), 2.68 (q, 2H, J=7.63 Hz), 1.51 (s, 9H), 1.25 (t, 3H, J=7.63 Hz), 0.95 (s, 9H), 0.10 (s, 6H).

tert-Butyl 4-({[tert-butyl(dimethyl)silyl]oxy}methyl)-6-ethylpyridin-2-ylcarbamate (0.352 g, 0.96 mmol) was dissolved in 2 mL $CH_2Cl_2$. tert-Butyl (dimethyl)silyl trifluoromethanesulfonate was added and the solution was stirred for 5.5 hours. N-Ethyl-N,N-diisopropylamine (0.669 mL, 3.84 mmol) was added and the solution was stirred for 0.5 hour. Saturated $NaHCO_3$ (aq) was added and the precipitate was extracted with $CH_2Cl_2$ (3×). The combined organic layers were dried ($Na_2SO_4$), filtered, and concentrated to afford a yellow oil. The oil was dissolved in 10 mL MeOH. Acetic acid (0.20 mL) was added and the solution was stirred for 0.5 hour. The reaction was concentrated in vacuo to afford an off white solid. The solid was purified by flash column chromatography (1:1 EtOAc/hexanes). The fractions containing the desired compound were concentrated to dryness to afford 12-1 as a colorless oil. $^1$H NMR ($CDCl_3$) δ 6.54 (s, 1H), 6.46 (s, 1H), 5.87 (bs, 2H), 4.65 (s, 2H), 2.73 (q, 2H, J=7.63 Hz), 1.29 (t, 3H, J=7.63 Hz), 0.95 (s, 9H), 0.12 (s, 6H).

2-{[4-({[tert-butyl(dimethyl)silyl]oxy}methyl)-6-ethylpyridin-2-yl]amino}-1,3-thiazole-5-carbonitrile (12-2)

4-({[tert-Butyl(dimethyl)silyl]oxy}methyl)-6-ethylpyridin-2-amine 12-1 (0.159 g, 0.60 mmol) was dissolved in 2 mL THF. 2-Chloro-1,3-thiazole-5-carbonitrile (0.103 g, 0.72 mmol) and sodium hydride (60% dispersion in mineral oil) (0.057 g, 2.38 mmol) were added and the solution was heated to 75° C. After 4 hours more 2-chloro-1,3-thiazole-5-carbonitrile (0.043 g, 0.30 mmol) and sodium hydride (0.014 g, 0.60 mmol) were added. After 5.5 hours more 2-chloro-1,3-thiazole-5-carbonitrile (0.086 g, 0.60 mmol) and sodium hydride (0.029 g, 1.19 mmol) were added. After 8.5 hours the solution was allowed to cool to room temperature. $H_2O$ was added and the reaction was concentrated in vacuo (to remove THF). 1N HCl was added to adjust to neutral pH. The resulting precipitate was filtered and washed with water to afford the desired compound 12-2 as a yellow solid. $^1$H NMR (DMSO-$d_6$) δ 12.23 (s, 1H), 8.25 (s, 1H), 6.70 (s, 1H), 6.83 (s, 1H), 4.73 (bs, 2H), 2.79 (q, 2H, J=7.63 Hz), 1.32 (t, 3H, J=7.63 Hz), 0.94 (s, 9H), 0.10 (s, 6H).

2-{[6-Ethyl-4-(hydroxymethyl)pyridin-2-yl]amino}-1,3-thiazole-5-carbonitrile (12-3)

2-{[4-({[tert-Butyl(dimethyl)silyl]oxy}methyl)-6-ethylpyridin-2-yl]amino}-1,3-thiazole-5-carbonitrile (12-2) (0.225 g, 0.60 mmol) was dissolved in 2 mL THF. Hydrogen fluoride-pyridine (Aldrich, HF ~70%, pyridine ~30%) (0.060 mL) was added. After 1.5 hours, additional hydrogen fluoride-pyridine (0.50 mL) was added. After 2.5 hours the reaction was concentrated to remove THF and the residue was diluted with 1M aqueous $K_2CO_3$. The resulting precipitate was filtered and washed with water to afford the desired compound 12-3 as a yellow solid. $^1$H NMR (DMSO-$d_6$) δ 12.19 (s, 1H), 8.26 (s, 1H), 6.96 (s, 1H), 6.86 (s, 1H), 4.51 (bs, 2H), 2.79 (q, 2H, J=7.63 Hz), 1.32 (t, 3H, J=7.63 Hz). [M+H]+=261.0816.

4-({2-[(5-cyano-1,3-thiazol-2-yl)amino]-6-ethylpyridin-4-yl}methyl)-N-methylpiperazine-1-carboxamide (12-4)

2-{[6-Ethyl-4-(hydroxymethyl)pyridin-2-yl]amino}-1,3-thiazole-5-carbonitrile (12-3, 0.146 g, 0.56 mmol) was stirred in anhydrous $CH_2Cl_2$ (2.5 mL) under $N_2$. N,N-Dimethylformamide (0.043 mL, 0.56 mmol) was added followed by phosphorous oxychloride (0.209 mL, 2.24 mmol). After 2.5 hours, the reaction was concentrated and quenched by the addition of saturated $NaHCO_3$ (aq). A precipitate formed which was filtered and washed with water to afford 2-{[4-(chloromethyl)-6-ethylpyridin-2-yl]amino}-1,3-thiazole-5-carbonitrile as an orange solid. $^1$H NMR (DMSO-$d_6$) δ 12.32 (s, 1H), 8.28 (s, 1H), 7.00 (d, 2H, J=3.66 Hz), 4.77 (s, 2H), 2.83 (q, 2H, J=7.63 Hz), 1.34 (t, 3H, J=7.63 Hz).

2-{[4-(Chloromethyl)-6-ethylpyridin-2-yl]amino}-1,3-thiazole-5-carbonitrile (0.113 g, 0.41 mmol) was dissolved in 2 mL DMSO. 1-[(Methylamino)carbonyl]piperazin-4-ium chloride (0.146 g, 0.81 mmol) and N-ethyl-N,N-diisopropylamine (0.283 mL, 1.63 mmol) were added and the solution was stirred for 24 hours. The reaction was diluted with water and the resulting precipitate was filtered and washed with water. The precipitate was purified by flash column chromatography (gradient, 5–10% MeOH/$CH_2Cl_2$). The fractions containing the desired compound were concentrated to dryness to afford the desired product 12-4.

$^1$H NMR (DMSO-$d_6$) δ 12.15 (bs, 1H), 8.39 (s, 1H), 8.25 (s, 1H), 6.95 (s, 1H), 6.88 (s, 1H), 6.42 (bd, 1H, J=4.62 Hz), 3.48 (s, 2H), 3.23 (m, 4H), 2.80 (q, 2H, J=7.63 Hz), 2.55 (d, 3H, J=4.31 Hz), 2.38 (m, 4H), 1.33 (t, 3H, J=7.63 Hz). [M+H]+=386.1747.

SCHEME 13

Synthesis of 2-({4-[(4-acetylpiperazin-1-yl)methyl]-6-methylpyridin-2-yl}amino)-1,3-thiazole-5-carbonitrile (13-4)

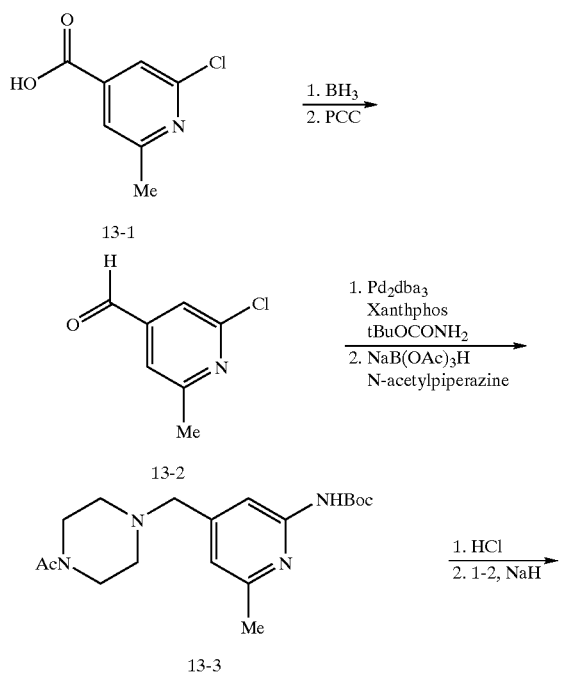

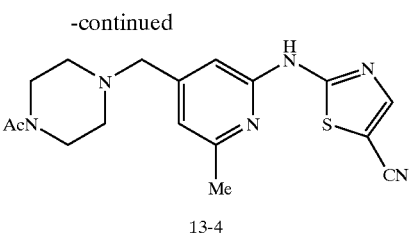

13-4

2-Chloro-6-methyl-pyridine-4-carbaldehyde (13-2)

2-Chloro-6-methyl-isonicotinic acid (13-1, 2.00 g, 11.7 mmol) was dissolved in 10 mL of anhydrous THF under $N_2$. The solution was cooled to 0° C., and borane-THF (1 M solution in THF, 14.0 mL, 14.0 mmol) was added slowly. The reaction was heated to reflux. After 3 hours the reaction was cooled to room temperature and quenched slowly with 1M HCl (aq) until cessation of bubbling. The pH of the solution was adjusted to 7 with saturated $NaHCO_3$ (aq). The mixture was extracted 3× with EtOAc and the extracts dried over $Na_2SO_4$, filtered and concentrated to afford (2-chloro-6-methyl-pyridin-4-yl)-methanol. $^1H$ NMR ($CDCl_3$) δ 7.16 (s, 1H), 7.06 (s, 1H), 4.70 (d, 2H, J=5.8 Hz), 2.53 (s, 3H), 1.95 (t, 1H, J=5.8 hz).

Pyridinium chlorochromate (3.09 g, 14.3 mmol) was stirred in 30 mL of DCM. (2-Chloro-6-methyl-pyridin-4-yl)-methanol (1.88 g, 11.9 mmol) was added and the reaction was stirred for 18 hours. The reaction was then diluted with 60 mL of diethylether. After stirring 10 minutes the reaction was filtered through a plug of celite and washed with diethylether. The filtrate was concentrated in vacuo to provide the titled compound, 13-2. $^1H$ NMR ($CDCl_3$) δ 10.01 (s, 1H), 7.56 (s, 1H), 7.49 (s, 1H), 2.66 (s, 3H).

tert-Butyl 4-[(4-acetylpiperazin-1-yl)methyl]-6-methylpyridin-2-ylcarbamate (13-3)

2-Chloro-6-methyl-pyridine-4-carbaldehyde (13-2, 0.609 g, 3.91 mmol), tert-butylcarbamate (0.550 g, 4.70 mmol), cesium carbonate (1.91 g, 5.87 mmol), tris (dibenzylideneacetone)dipalladium(0) (0.036 g, 0.040 mmol) and Xantphos (0.068 g, 0.030 mmol) were stirred in 10 mL of anhydrous dioxane under $N_2$. The reaction was heated to 80° C. and after 18 hours the reaction was cooled to room temperature. The mixture was diluted with water and extracted 3× with EtOAc. The extracts were dried over $Na_2SO_4$, filtered and concentrated. Purification by flash column chromatography afforded impure tert-butyl 4-formyl-6-methylpyridin-2-ylcarbamate. This aldehyde was dissolved in 2 mL of 1,2-dichloroethane. N-Acetylpiperazine (0.074 g, 0.58 mmol) was added followed by addition of 0.05 mL HOAc and $NaBH(OAc)_3$ (0.122 g, 0.58 mmol). After 3 hours the reaction was quenched by the addition of half-saturated $NaHCO_3$ (aq). The mixture was extracted 3× with DCM (dichloromethane) and the extracts were dried over $Na_2SO_4$, filtered and concentrated to afford the titled compound, 13-3. $^1H$ NMR ($CDCl_3$) δ 7.67 (s, 1H), 7.47 (s, 1H), 6.84 (s, 1H), 3.64 (t, 2H, J=4.9 Hz), 3.47 (m, 4H), 2.44 (m, 7H), 2.09 (s, 3H), 1.51 (s, 9H).

2-({4-[(4-acetylpiperazin-1-yl)methyl]-6-methylpyridin-2-yl}amino)-1,3-thiazole-5-carbonitrile (13-4)

tert-Butyl 4-[(4-acetylpiperazin-1-yl)methyl]-6-methylpyridin-2-ylcarbamate (13-3) was dissolved in $CH_2Cl_2$ and the solution was cooled to 0° C. 4.0M HCl in dioxane was added and the solution allowed to warm to room temperature. The reaction was concentrated in vacuo to afford 1-acetyl-4-[(2-amino-6-methylpyridin-4-yl)methyl]piperazin-4-ium chloride. 1-Acetyl-4-[(2-amino-6-methylpyridin-4-yl)methyl]piperazin-4-ium chloride (0.095 g, 0.30 mmol) was dissolved in 2 mL THF. 2-Chloro-1,3-thiazole-5-carbonitrile (0.051 g, 0.36 mmol) and sodium hydride (60% dispersion in mineral oil) (0.028 g, 1.19 mmol) were added and the solution was heated to 75° C. After 4 hours more 2-chloro-1,3-thiazole-5-carbonitrile (0.051 g, 0.36 mmol) was added. After 5.5 hours the solution was allowed to cool to room temperature and concentrated in vacuo. Acetic acid (0.070 mL, 1.19 mmol) was added and was concentrated in vacuo. The residue was purified by reverse phase chromatography (gradient, 5–100% $CH_3CN$/$H_2O$+0.1% TFA). The fractions containing the desired compound were concentrated to dryness to afford the TFA salt of 13-4. TFA salt: $^1H$ NMR ($CD_3OD$) δ 8.04 (s, 1H), 6.99 (s, 1H), 6.95 (s, 1H), 4.13 (bs, 2H), 3.74 (bs, 2H), 3.06 (bs, 6H), 2.61 (s, 3H), 2.13 (s, 3H). [M+H]+=357.1494.

What is claimed is:

1. A compound of Formula I:

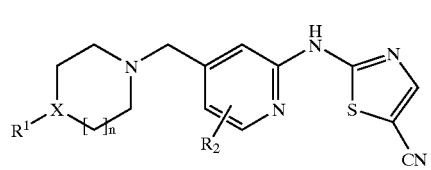

I or a pharmaceutically acceptable salt or stereoisomer thereof, wherein n is 1;

X is N, $R^1$ is
   2) (C=O)$NR^3H$, $R^2$ is
   1) H,
   2) OH,
   3) $OC_1$–$C_6$ alkyl,
   4) $C_1$–$C_6$ alkyl, or
   5) halo; and $R^3$ is $C_1$–$C_6$ alkyl.

2. A compound selected from:

4-[2-(5-cyano-thiazol-2-ylamino)-pyridin-4-ylmethyl]-piperazine-1-carboxylic acid methylamide;

2-[(4-{[4-(methylsulfonyl)piperidin-1-yl]methyl}pyridin-2-yl)amino]-1,3-thiazole-5-carbonitrile;

N-[(3R)-1-({2-[(5-cyano-1,3-thiazol-2-yl)amino]pyridin-4-yl}methyl)pyrrolidin-3-yl]-N'-methylurea;

2-{[4-({[(3R)-5-oxopyrrolidin-3-yl]amino}methyl)pyridin-2-yl]amino}-1,3-thiazole-5-carbonitrile;

4-[2-(5-cyano-thiazol-2-ylamino)-5-methyl-pyridin-4-ylmethyl]-piperazine-1-carboxylic acid methylamide;

4-[2-(5-cyano-thiazol-2-ylamino)-3-methyl-pyridin-4-ylmethyl]-piperazine-1-carboxylic acid methylamide;

4-({2-chloro-6-[(5-cyano-1,3-thiazol-2-yl)amino]pyridin-4-yl}methyl)-N-methylpiperazine-1-carboxamide;

4-({2-[(5-cyano-1,3-thiazol-2-yl)amino]-6-ethylpyridin-4-yl}methyl)-N-methylpiperazine-1-carboxamide; and 2-({4-[(4-acetylpiperazin-1-yl)methyl]-6-methylpyridin-2-yl}amino)-1,3-thiazole-5-carbonitrile;

or a pharmaceutically acceptable salt or stereoisomer thereof.

3. A compound which is:

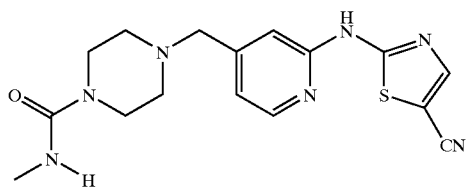

4-[2-(5-cyano-thiazol-2-ylamino)-pyridin-4-ylmethyl]-piperazine-1-carboxylic acid methylamide, or a pharmaceutically acceptable salt thereof.

4. A compound which is:

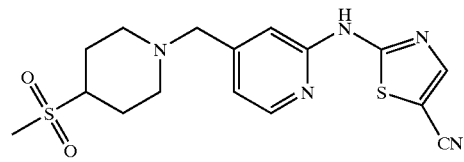

2-[(4-{[4-(methylsulfonyl)piperidin-1-yl]methyl}pyridin-2-yl)amino]-1,3-thiazole-5-carbonitrile, or a pharmaceutically acceptable salt thereof.

5. A compound which is:

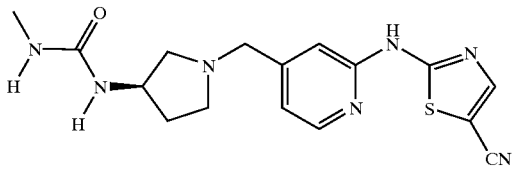

N-[(3R)-1-({2-[(5-cyano-1,3-thiazol-2-yl)amino]pyridin-4-yl}methyl)pyrrolidin-3-yl]-N'-methylurea, or a pharmaceutically acceptable salt or stereoisomer thereof.

6. A compound which is:

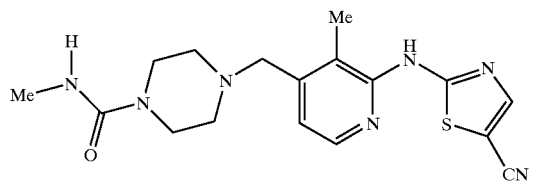

4-[2-(5-cyano-thiazol-2-ylamino)-3-methyl-pyridin-4-ylmethyl]-piperazine-1-carboxylic acid methylamide, or a pharmaceutically accepatble salt thereof.

7. A pharmaceutical composition which is comprised of a compound in accordance with claim 1 and a pharmaceutically acceptable carrier.

* * * * *